United States Patent
Yoon et al.

(10) Patent No.: US 11,229,677 B2
(45) Date of Patent: *Jan. 25, 2022

(54) ANTIBACTERIAL COMPOSITION AND A METHOD OF TREATING STAPHYLOCOCCAL INFECTIONS WITH THE ANTIBACTERIAL COMPOSITION

(71) Applicant: INTRON BIOTECHNOLOGY, INC., Seongnam-Si (KR)

(72) Inventors: Seong Jun Yoon, Seoul (KR); Soo Youn Jun, Seoul (KR); Gi Mo Jung, Seoul (KR); Sang Hyeon Kang, Seoul (KR)

(73) Assignee: INTRON BIOTECHNOLOGY, INC., Seongnam-si (KR)

( * ) Notice: Subject to any disclaimer, the term of this patent is extended or adjusted under 35 U.S.C. 154(b) by 67 days.

This patent is subject to a terminal disclaimer.

(21) Appl. No.: 16/300,566

(22) PCT Filed: Jan. 9, 2017

(86) PCT No.: PCT/IB2017/050087
§ 371 (c)(1),
(2) Date: Nov. 10, 2018

(87) PCT Pub. No.: WO2017/122111
PCT Pub. Date: Jul. 20, 2017

(65) Prior Publication Data
US 2019/0282657 A1     Sep. 19, 2019

Related U.S. Application Data

(60) Provisional application No. 62/277,506, filed on Jan. 12, 2016.

(51) Int. Cl.
| | | |
|---|---|---|
| *A61K 38/16* | (2006.01) | |
| *A61P 31/04* | (2006.01) | |
| *A61K 47/26* | (2006.01) | |
| *A61K 47/10* | (2017.01) | |
| *A61K 9/08* | (2006.01) | |
| *A61K 9/00* | (2006.01) | |
| *A61K 47/18* | (2017.01) | |

(52) U.S. Cl.
CPC ............ *A61K 38/16* (2013.01); *A61K 9/0019* (2013.01); *A61K 9/08* (2013.01); *A61K 47/10* (2013.01); *A61K 47/183* (2013.01); *A61K 47/26* (2013.01); *A61P 31/04* (2018.01)

(58) Field of Classification Search
None
See application file for complete search history.

(56) References Cited

U.S. PATENT DOCUMENTS

| 8,232,370 B2 | 7/2012 | Yoon et al. |
|---|---|---|
| 2010/0004321 A1 | 1/2010 | Ross et al. |
| 2010/0172918 A1 | 7/2010 | Yoon et al. |
| 2015/0224179 A1 | 8/2015 | Yoon et al. |
| 2019/0183803 A1* | 6/2019 | Yoon ................ A61K 47/10 |

FOREIGN PATENT DOCUMENTS

| WO | 9704801 A1 | 2/1997 | |
|---|---|---|---|
| WO | WO-2008016240 A1 * | 2/2008 | ........... C07K 14/005 |
| WO | 2009035303 A2 | 3/2009 | |
| WO | WO-2013180316 A1 * | 12/2013 | ............... C12N 7/00 |

OTHER PUBLICATIONS

Liao et al. "Removal of N-terminal methionine from recombinant proteins by engineered *E. coli* methionine aminopeptidase" Protein Science 13:1802-1810. (Year: 2005).*
Burdette et al. "*Staphylococcus aureus* pyomyositis compared with non-*Staphylococcus aureus* pyomyositis" Journal of Infections 64:507-512. (Year: 2012).*
Gosbell I B "Diagnosis and management of catheter-related bloodstream infections due to *Staphylococcus aureus*" Internal Medicine Journal 35:S45-S62. (Year: 2005).*
Akashi et al., Effect of N-methionine-free, bacterially synthesized recombinant human granulocyte-macrophage colony-stimulating factor in a primate model, Eur. J. Haematol, 1990: 44: 99-104.
Lipiainen et al., Formulation and stability of cytokine therapeutics, Journal of Pharmaceutical Sciences, 104: 307-326, 2015 (published online Dec. 9, 2014).
Gilmer et al., "Novel bacteriophage lysin with broad lytic activity protects against mixed infection by *Streptococcus pyogenese* and methicillin-resistant *Staphylococcus aureus*" Antimicrobial Agents and Chemotherapy, vol. 57, No. 6, pp. 2743-2750 (2013).
NCBI, GenPept accession No. YP_0070021294.1 (Nov. 16, 2012).

* cited by examiner

*Primary Examiner* — Sudhakar Katakam
*Assistant Examiner* — Zachary J Miknis
(74) *Attorney, Agent, or Firm* — SIMI Law Group, P.C.

(57) ABSTRACT

A method of treating staphylococcal infections includes administering to a subject an effective amount of an antibacterial composition having a broad bactericidal activity. The antibacterial composition includes a first antibacterial protein consisting of the amino acid sequence as set forth in SEQ. ID. NO: 1 and/or a second antibacterial protein consisting of the amino acid sequence as set forth in SEQ. ID. NO: 2.

7 Claims, 11 Drawing Sheets

Specification includes a Sequence Listing.

*Staphylococcus cohnii*

Strain: KCTC 3574 (ATCC 49330)

(A) Spot-on-lawn assay

(B) Turbidity reduction assay (0.5 μg/ml)

$TOD_{50} = 15.0$

*Staphylococcus delphini*

Strain: KCTC 3592 (ATCC 49171)

(A) Spot-on-lawn assay

(B) Turbidity reduction assay (0.1 μg/ml)

$TOD_{50} = 4.6$

*Staphylococcus lugdunensis*
Strain: CCARM 3734

(A) Spot-on-lawn assay
(B) Turbidity reduction assay (0.1 μg/ml)

$TOD_{50} = 7.4$

*Staphylococcus muscae*
Strain: KCTC 3576 (ATCC 49910)

(A) Spot-on-lawn assay
(B) Turbidity reduction assay (0.1 μg/ml)

$TOD_{50} = 9.5$

SEQUENCE LISTING

<160> NUMBER OF SEQ ID NOS: 3

<210> SEQ ID NO 1
<211> LENGTH: 495
<212> TYPE: PRT
<213> ORGANISM: Artificial Sequence
<220> FEATURE:
<223> OTHER INFORMATION: antibacterial composition

<400> SEQUENCE: 1

Met Ala Lys Thr Gln Ala Glu Ile Asn Lys Arg Leu Asp Ala Tyr Ala
1               5                   10                  15

Lys Gly Thr Val Asp Ser Pro Tyr Arg Ile Lys Lys Ala Thr Ser Tyr
                20                  25                  30

Asp Pro Ser Phe Gly Val Met Glu Ala Gly Ala Ile Asp Ala Asp Gly
            35                  40                  45

Tyr Tyr His Ala Gln Cys Gln Asp Leu Ile Thr Asp Tyr Val Leu Trp
        50                  55                  60

Leu Thr Asp Asn Lys Val Arg Thr Trp Gly Asn Ala Lys Asp Gln Ile
65                  70                  75                  80

Lys Gln Ser Tyr Gly Thr Gly Phe Lys Ile His Glu Asn Lys Pro Ser
                85                  90                  95

Thr Val Pro Lys Lys Gly Trp Ile Ala Val Phe Thr Ser Gly Ser Tyr
            100                 105                 110

Gln Gln Trp Gly His Ile Gly Ile Val Tyr Asp Gly Gly Asn Thr Ser
        115                 120                 125

Thr Phe Thr Ile Leu Glu Gln Asn Trp Asn Gly Tyr Ala Asn Lys Lys
130                 135                 140

Pro Thr Lys Arg Val Asp Asn Tyr Tyr Gly Leu Thr His Phe Ile Glu
145                 150                 155                 160

Ile Pro Val Lys Ala Gly Thr Thr Val Lys Lys Glu Thr Ala Lys Lys
                165                 170                 175

Ser Ala Ser Lys Thr Pro Ala Pro Lys Lys Lys Ala Thr Leu Lys Val
            180                 185                 190

Ser Lys Asn His Ile Asn Tyr Thr Met Asp Lys Arg Gly Lys Lys Pro
        195                 200                 205

Glu Gly Met Val Ile His Asn Asp Ala Gly Arg Ser Ser Gly Gln Gln
210                 215                 220

Tyr Glu Asn Ser Leu Ala Asn Ala Gly Tyr Ala Arg Tyr Ala Asn Gly
225                 230                 235                 240

Ile Ala His Tyr Tyr Gly Ser Glu Gly Tyr Val Trp Glu Ala Ile Asp
                245                 250                 255

Ala Lys Asn Gln Ile Ala Trp His Thr Gly Asp Gly Thr Gly Ala Asn
            260                 265                 270

Ser Gly Asn Phe Arg Phe Ala Gly Ile Glu Val Cys Gln Ser Met Ser
        275                 280                 285

Ala Ser Asp Ala Gln Phe Leu Lys Asn Glu Gln Ala Val Phe Gln Phe
290                 295                 300

Thr Ala Glu Lys Phe Lys Glu Trp Gly Leu Thr Pro Asn Arg Lys Thr
305                 310                 315                 320

Val Arg Leu His Met Glu Phe Val Pro Thr Ala Cys Pro His Arg Ser
                325                 330                 335

Met Val Leu His Thr Gly Phe Asn Pro Val Thr Gln Gly Arg Pro Ser
            340                 345                 350

Gln Ala Ile Met Asn Lys Leu Lys Asp Tyr Phe Ile Lys Gln Ile Lys

```
            355                 360                 365
Asn Tyr Met Asp Lys Gly Thr Ser Ser Thr Val Val Lys Asp Gly
            370                 375                 380

Lys Thr Ser Ser Ala Ser Thr Pro Ala Thr Arg Pro Val Thr Gly Ser
385                 390                 395                 400

Trp Lys Lys Asn Gln Tyr Gly Thr Trp Tyr Lys Pro Glu Asn Ala Thr
                405                 410                 415

Phe Val Asn Gly Asn Gln Pro Ile Val Thr Arg Ile Gly Ser Pro Phe
            420                 425                 430

Leu Asn Ala Pro Val Gly Gly Asn Leu Pro Ala Gly Ala Thr Ile Val
            435                 440                 445

Tyr Asp Glu Val Cys Ile Gln Ala Gly His Ile Trp Ile Gly Tyr Asn
            450                 455                 460

Ala Tyr Asn Gly Asn Arg Val Tyr Cys Pro Val Arg Thr Cys Gln Gly
465                 470                 475                 480

Val Pro Pro Asn His Ile Pro Gly Val Ala Trp Gly Val Phe Lys
                485                 490                 495

<210> SEQ ID NO 2
<211> LENGTH: 494
<212> TYPE: PRT
<213> ORGANISM: Artificial Sequence
<220> FEATURE:
<223> OTHER INFORMATION: antibacterial composition

<400> SEQUENCE: 2

Ala Lys Thr Gln Ala Glu Ile Asn Lys Arg Leu Asp Ala Tyr Ala Lys
1               5                   10                  15

Gly Thr Val Asp Ser Pro Tyr Arg Ile Lys Lys Ala Thr Ser Tyr Asp
                20                  25                  30

Pro Ser Phe Gly Val Met Glu Ala Gly Ala Ile Asp Ala Asp Gly Tyr
            35                  40                  45

Tyr His Ala Gln Cys Gln Asp Leu Ile Thr Asp Tyr Val Leu Trp Leu
50                  55                  60

Thr Asp Asn Lys Val Arg Thr Trp Gly Asn Ala Lys Asp Gln Ile Lys
65                  70                  75                  80

Gln Ser Tyr Gly Thr Gly Phe Lys Ile His Glu Asn Lys Pro Ser Thr
                85                  90                  95

Val Pro Lys Lys Gly Trp Ile Ala Val Phe Thr Ser Gly Ser Tyr Gln
            100                 105                 110

Gln Trp Gly His Ile Gly Ile Val Tyr Asp Gly Gly Asn Thr Ser Thr
            115                 120                 125

Phe Thr Ile Leu Glu Gln Asn Trp Asn Gly Tyr Ala Asn Lys Lys Pro
130                 135                 140

Thr Lys Arg Val Asp Asn Tyr Tyr Gly Leu Thr His Phe Ile Glu Ile
145                 150                 155                 160

Pro Val Lys Ala Gly Thr Thr Val Lys Lys Glu Thr Ala Lys Lys Ser
                165                 170                 175

Ala Ser Lys Thr Pro Ala Pro Lys Lys Lys Ala Thr Leu Lys Val Ser
            180                 185                 190

Lys Asn His Ile Asn Tyr Thr Met Asp Lys Arg Gly Lys Lys Pro Glu
            195                 200                 205

Gly Met Val Ile His Asn Asp Ala Gly Arg Ser Ser Gly Gln Gln Tyr
210                 215                 220

Glu Asn Ser Leu Ala Asn Ala Gly Tyr Ala Arg Tyr Ala Asn Gly Ile
```

```
                225                 230                 235                 240
Ala His Tyr Tyr Gly Ser Glu Gly Tyr Val Trp Glu Ala Ile Asp Ala
                    245                 250                 255

Lys Asn Gln Ile Ala Trp His Thr Gly Asp Gly Thr Gly Ala Asn Ser
                260                 265                 270

Gly Asn Phe Arg Phe Ala Gly Ile Glu Val Cys Gln Ser Met Ser Ala
                275                 280                 285

Ser Asp Ala Gln Phe Leu Lys Asn Glu Gln Ala Val Phe Gln Phe Thr
            290                 295                 300

Ala Glu Lys Phe Lys Glu Trp Gly Leu Thr Pro Asn Arg Lys Thr Val
305                 310                 315                 320

Arg Leu His Met Glu Phe Val Pro Thr Ala Cys Pro His Arg Ser Met
                    325                 330                 335

Val Leu His Thr Gly Phe Asn Pro Val Thr Gln Gly Arg Pro Ser Gln
                340                 345                 350

Ala Ile Met Asn Lys Leu Lys Asp Tyr Phe Ile Lys Gln Ile Lys Asn
                355                 360                 365

Tyr Met Asp Lys Gly Thr Ser Ser Thr Val Val Lys Asp Gly Lys
            370                 375                 380

Thr Ser Ser Ala Ser Thr Pro Ala Thr Arg Pro Val Thr Gly Ser Trp
385                 390                 395                 400

Lys Lys Asn Gln Tyr Gly Thr Trp Tyr Lys Pro Glu Asn Ala Thr Phe
                    405                 410                 415

Val Asn Gly Asn Gln Pro Ile Val Thr Arg Ile Gly Ser Pro Phe Leu
                420                 425                 430

Asn Ala Pro Val Gly Gly Asn Leu Pro Ala Gly Ala Thr Ile Val Tyr
                435                 440                 445

Asp Glu Val Cys Ile Gln Ala Gly His Ile Trp Ile Gly Tyr Asn Ala
                    450                 455                 460

Tyr Asn Gly Asn Arg Val Tyr Cys Pro Val Arg Thr Cys Gln Gly Val
465                 470                 475                 480

Pro Pro Asn His Ile Pro Gly Val Ala Trp Gly Val Phe Lys
                    485                 490

<210> SEQ ID NO 3
<211> LENGTH: 1488
<212> TYPE: DNA
<213> ORGANISM: Artificial Sequence
<220> FEATURE:
<223> OTHER INFORMATION: antibacterial composition

<400> SEQUENCE: 3
atggctaaga ctcaagcaga aataaataaa cgtttagacg cttatgcaaa aggtacagta      60
gacagtcctt atagaattaa aaaagctaca agctatgacc catcgtttgg tgtaatggaa     120
gcaggagcaa ttgacgcaga tggttactat catgcacagt gccaagactt aattactgat     180
tatgtattat ggttaacaga taataaagtt agaacttggg gtaatgctaa agaccaaatc     240
aaacaaagtt atggtactgg atttaaaata catgaaaata accttctac agtacctaaa      300 aaaggatgga ttgctgtatt tacatccggt agttatcagc aatggggtca cataggtatt     360
gtatatgatg gaggtaatac ttctacattt actatttag agcaaaactg gaacggttac      420
gctaataaaa aacctacaaa acgtgtagat aattattacg gattaactca ttttattgag     480
atacctgtaa aagcaggaac tactgttaaa aagaaacag ctaagaaaag tgcaagtaaa      540
acacctgcac ctaaaaagaa agcaacacta aaagtttcta agaaccatat taactataca     600
```

```
atggataaac gtggtaagaa acctgaagga atggtaatac acaacgatgc aggtcgttct      660
tcagggcaac aatacgagaa ttcattagct aacgcaggtt atgctagata tgctaatggt      720
attgctcatt actatggctc tgaaggttat gtatgggaag caatagatgc taagaatcaa      780
attgcttggc acacaggaga tggaacagga gcaaactcag gtaactttag atttgcaggt      840
attgaagtct gtcaatcaat gagtgctagt gatgctcaat tccttaaaaa cgaacaagca      900
gtattccaat ttactgcaga gaaatttaaa gaatggggtc ttactcctaa tcgtaaaact      960
gtaagattgc atatggaatt tgttccaaca gcttgtcctc atcgttctat ggttcttcat     1020
acaggattta atccagtaac acaaggaaga ccatctcaag caataatgaa taaactaaaa     1080
gattatttca ttaaacaaat taaaaactac atggataaag gaacttcaag ttctacagta     1140
gttaaagacg gtaaaacaag tagcgcaagt acaccggcaa ctagaccagt aacaggctct     1200
tggaaaaaga accagtacgg aacttggtac aaaccggaaa atgcaacatt tgttaatggt     1260
aaccaaccta tagtaactag aataggttct ccattcttaa atgctccagt aggaggtaac     1320
ttaccggcag gagctacaat tgtatatgac gaagtttgta tccaagcagg tcacatttgg     1380
ataggttaca atgcttacaa tggtaacaga gtatattgcc ctgttagaac ttgtcaagga     1440
gttccaccta atcatatacc tggggttgcc tggggagtat tcaaatag              1488
```

ANTIBACTERIAL COMPOSITION AND A METHOD OF TREATING STAPHYLOCOCCAL INFECTIONS WITH THE ANTIBACTERIAL COMPOSITION

The present application is the national stage application of PCT/IB2017/050087, filed on Jan. 9, 2017, which claims the benefit of U.S. Provisional Application No. 62/277,506, filed on Jan. 12, 2016, which is incorporated by reference for all purposes as if fully set forth herein.

BACKGROUND OF THE INVENTION

Field of the Invention

The present invention relates to an antibacterial composition and a method of treating staphylococcal infections with the antibacterial composition.

Discussion of the Related Art

*Staphylococcus* is a genus of Gram-positive bacteria, and can cause a wide variety of diseases in humans and animals through either toxin production or penetration. *Staphylococcus*-related illness can range from mild and requiring no treatment to severe and potentially fatal. Over 30 different species of *Staphylococcus* can infect humans. Manifestations of staphylococcal infections usually depend on the type of infection the organism causes. Common types of infections include the followings: skin infections (e.g., folliculitis, furuncles, impetigo, wound infections, scalded skin syndrome), soft-tissue infections (e.g., pyomyositis, septic bursitis, septic arthritis), toxic shock syndrome, purpura fulminans, endocarditis, osteomyelitis, pneumonia, infections related to prosthetic devices (e.g., prosthetic joints and heart valves; vascular shunts, grafts, catheters), and urinary tract infection. People with suppressed immune systems (those taking immune-suppressing medications or with immune deficiencies) are at increased risk for developing more serious infections.

Staphylococcal infections are usually caused by *Staphylococcus aureus*. The infections due to other *Staphylococcus* species have been steadily rising. For example, *Staphylococcus saprophyticus* accounts for up to 10% of uncomplicated urinary tract infections in young women; *Staphylococcus schleiferi*, *Staphylococcus lugdunensis* and *Staphylococcus haemolyticus* are associated with native valve endocarditis. Coagulase-negative *Staphylococcus* (CoNS) has emerged as a clinically relevant pathogen found in more than 12% of hospitalized inpatients and implicated in up to 30% of healthcare-associated sepsis cases. In addition, many *Staphylococcus* species are resistant to many antibiotics.

Considering the problems causing by *Staphylococcus*, it is urgently requested to develop a method for treating staphylococcal infections caused by antibiotic-sensitive and antibiotic-resistant *Staphylococcus*. Even though antibiotics are still major therapeutic agents for the treatment of such staphylococcal infections, the antibiotic-based treatment has serious problems such as the reduced treatment outcome. Therefore, to enhance the treatment efficiency for staphylococcal infections, a new efficient alternative (therapeutic agent) is urgently requested.

Recently, the use of endolysins has drawn our attention as a new way of treating bacterial infections. Phage endolysins, also known as phage lysins or lysins, are bacteriophage-encoded, peptidoglycan-degrading enzymes that rapidly degrade bacterial cell walls and release phage progeny. U.S. Pat. No. 8,232,370 reported that an antibacterial protein that has antibacterial activity specific to *Staphylococcus aureus*.

Furthermore, it is widely reported that endolysins have species-specific bactericidal activity. For example, Future Microbiol. 2012 October; 7(10): 1147-1171 at 1148 reports that "[a]n important advantage of endolysins over classical antibiotics is their high specificity for certain PG [peptidoglycan] types, which generally limits their antimicrobial action to members of a certain bacterial genus, species or even serotype." Applied and Environmental Microbiology, March 2009, p. 1388-1394, at pages 1388-1389, reports that "[bacteriophage lysins] not only exert their lethal effects in the absence of bacteriophage (cause 'lysis from without') but also display specificity for a bacterial host, often for a particular genus, species, or even a subspecies depending on the lysin." Applied and Environmental Microbiology, November 2002, p. 5311-5317, at page 5311, reports that "[a]ll 48 tested strains of *C. perfringens* were sensitive to the murein hydrolase [of the Bacteriophage φ3626 Dual Lysis System], whereas other clostridia and bacteria belonging to other genera were generally not affected."

Therefore, there is a need to develop antibacterial proteins that have antibacterial activity specific to more than one *Staphylococcus* species, and thus the infections caused by multiple *Staphylococcus* species can be treated.

SUMMARY OF THE INVENTION

The present invention provides a method of treating staphylococcal infections. The method includes administering to a subject an effective amount of an antibacterial composition having a broad bactericidal activity against at least one of or all following *Staphylococcus* species: *Staphylococcus arlettae, Staphylococcus aureus, Staphylococcus auricularis, Staphylococcus carnosus, Staphylococcus carprae, Staphylococcus chromogenes, Staphylococcus cohnii, Staphylococcus delphini, Staphylococcus epidermidis, Staphylococcus equorum, Staphylococcus gallinarum, Staphylococcus hemolyticus, Staphylococcus hominis, Staphylococcus intermedius, Staphylococcus kloosii, Staphylococcus lentus, Staphylococcus lugdunensis, Staphylococcus muscae, Staphylococcus pasteuri, Staphylococcus saprophyticus, Staphylococcus warneri*, and *Staphylococcus xylosus*. The antibacterial composition includes a first antibacterial protein consisting of the amino acid sequence as set forth in SEQ. ID. NO: 1 and/or a second antibacterial protein consisting of the amino acid sequence as set forth in SEQ. ID. NO: 2.

In an aspect, the antibacterial composition includes 15-35 mole % of the first antibacterial protein and 55-85 mole % of the second antibacterial protein.

In another aspect, the antibacterial composition includes 25 mole % of the first antibacterial protein and 75 mole % of the second antibacterial protein.

In another aspect, the staphylococcal infections are skin infections, soft-tissue infections, toxic shock syndrome, purpura fulminans, endocarditis, osteomyelitis, pneumonia, infections related to prosthetic devices, or urinary tract infections.

In another aspect, the skin infections are folliculitis, furuncles, impetigo, wound infections, or scalded skin syndrome.

In another aspect, the soft-tissue infections are pyomyositis, septic bursitis, or septic arthritis.

In another aspect, the prosthetic devices are prosthetic joints and heart valves, vascular shunts, grafts, or catheters.

The present invention provides an antibacterial protein consisting of the amino acid sequence as set forth in SEQ. ID. NO: 1. The antibacterial protein has a broad bactericidal activity against at least one of or all following *Staphylococcus* species: *Staphylococcus arlettae, Staphylococcus aureus, Staphylococcus auricularis, Staphylococcus carnosus, Staphylococcus carprae, Staphylococcus chromogenes, Staphylococcus cohnii, Staphylococcus delphini, Staphylococcus epidermidis, Staphylococcus equorum, Staphylococcus gallinarum, Staphylococcus hemolyticus, Staphylococcus hominis, Staphylococcus intermedius, Staphylococcus kloosii, Staphylococcus lentus, Staphylococcus lugdunensis, Staphylococcus muscae, Staphylococcus pasteuri, Staphylococcus saprophyticus, Staphylococcus warneri,* and *Staphylococcus xylosus.*

In an aspect, a pharmaceutical composition for treating staphylococcal infections includes the antibacterial protein as an active ingredient.

The present invention provides an antibacterial protein consisting of the amino acid sequence as set forth in SEQ. ID. NO: 2. The antibacterial protein has a broad bactericidal activity against at least one of or all the following *Staphylococcus* species: *Staphylococcus arlettae, Staphylococcus aureus, Staphylococcus auricularis, Staphylococcus carnosus, Staphylococcus carprae, Staphylococcus chromogenes, Staphylococcus cohnii, Staphylococcus delphini, Staphylococcus epidermidis, Staphylococcus equorum, Staphylococcus gallinarum, Staphylococcus hemolyticus, Staphylococcus hominis, Staphylococcus intermedius, Staphylococcus kloosii, Staphylococcus lentus, Staphylococcus lugdunensis, Staphylococcus muscae, Staphylococcus pasteuri, Staphylococcus saprophyticus, Staphylococcus warneri,* and *Staphylococcus xylosus.*

In an aspect, a pharmaceutical composition for treating staphylococcal infections includes the antibacterial protein as an active ingredient.

The present invention provides an antibacterial composition including a first antibacterial protein consisting of the amino acid sequence as set forth in SEQ. ID. NO: 1 and a second antibacterial protein consisting of the amino acid sequence as set forth in SEQ. ID. NO: 2. The antibacterial composition has a broad bactericidal activity against at least one of or all following *Staphylococcus* species: *Staphylococcus arlettae, Staphylococcus aureus, Staphylococcus auricularis, Staphylococcus carnosus, Staphylococcus carprae, Staphylococcus chromogenes, Staphylococcus cohnii, Staphylococcus delphini, Staphylococcus epidermidis, Staphylococcus equorum, Staphylococcus gallinarum, Staphylococcus hemolyticus, Staphylococcus hominis, Staphylococcus intermedius, Staphylococcus kloosii, Staphylococcus lentus, Staphylococcus lugdunensis, Staphylococcus muscae, Staphylococcus pasteuri, Staphylococcus saprophyticus, Staphylococcus warneri,* and *Staphylococcus xylosus.*

In an aspect, the antibacterial composition includes 15-35 mole % of the first antibacterial protein and 55-85 mole % of the second antibacterial protein.

In another aspect, the antibacterial composition includes 25 mole % of the first antibacterial protein and 75 mole % of the second antibacterial protein.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE ILLUSTRATED EMBODIMENTS

Figure 1:
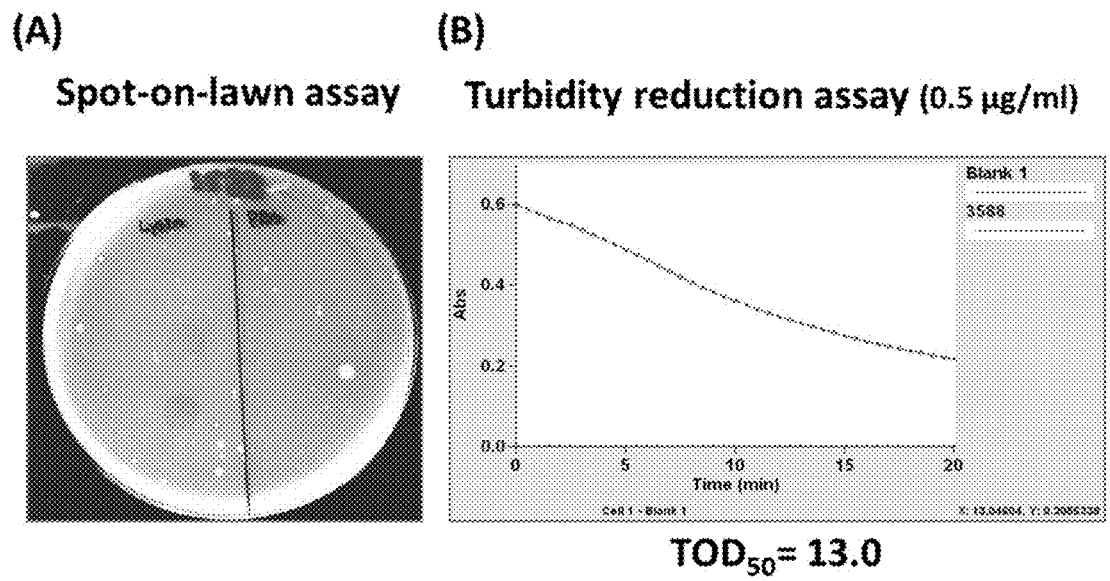
FIG. 1 is a result showing the effective bactericidal activity against *Staphylococcus arlettae*. (A) spot-on-lawn assay and (B) turbidity reduction assay.

Reference will now be made in detail to embodiments of the present invention, example of which is illustrated in the accompanying drawings.

As used herein, "effective amount" means an amount of a composition (as applicable) sufficient to significantly induce a positive effect (e.g., improvement in skin infections, soft-tissue infections, etc.) but low enough to avoid serious side effects (e.g., undue toxicity or allergic reaction). "At least one of or all the following *Staphylococcus* species" means any one, two, three, four, five, six . . . up to twenty-two *Staphylococcus* species selected from the group consisting of *Staphylococcus arlettae*, *Staphylococcus aureus*, *Staphylococcus auricularis*, *Staphylococcus carnosus*, *Staphylococcus carprae*, *Staphylococcus chromogenes*, *Staphylococcus cohnii*, *Staphylococcus delphini*, *Staphylococcus epidermidis*, *Staphylococcus equorum*, *Staphylococcus gallinarum*, *Staphylococcus hemolyticus*, *Staphylococcus hominis*, *Staphylococcus intermedius*, *Staphylococcus kloosii*, *Staphylococcus lentus*, *Staphylococcus lugdunensis*, *Staphylococcus muscae*, *Staphylococcus pasteuri*, *Staphylococcus saprophyticus*, *Staphylococcus warneri*, and *Staphylococcus xylosus*.

An antibacterial composition has bactericidal activity against various *Staphylococcus* strains and selectively induces bacteriolysis of various *Staphylococcus* strains and the composition contains one or more antibacterial proteins having a broad bactericidal activity (lytic activity) spectrum against various *Staphylococcus* strains as active ingredient.

The antibacterial proteins having a broad bactericidal activity (lytic activity) spectrum against various *Staphylococcus* strains have the amino acid sequences represented by SEQ. ID. NO: 1 and SEQ. ID. NO: 2. The antibacterial protein having the amino acid sequence of SEQ. ID. NO: 2. is believed to be the posttranslationally modified form (i.e., the initiator methionine deleted form) of the antibacterial protein having the amino acid sequence of SEQ. ID. NO: 1.

It is known that the three dimensional structure, bioactivity and stability may differ between a molecule with methionine at its amino terminus and one without methionine, even though both molecules are otherwise the same protein. It is also believed that the addition of methionine at the amino terminus may cause an increase in protein antigenicity. Therefore, it would be important, in industrial application, to establish a relatively simple and efficient method of selectively removing such amino terminal methionine.

In prior methods for solving this problem, a process was suggested by which methionine could be removed by cyanogen bromide (BrCN) cleavage; however, no satisfactory result has been obtained, since the process not only premises the absence of other methionine residues in the molecule of the required mature protein but also subjects the protein to a drastic chemical reaction.

The antibacterial composition of the present invention advantageously has the posttranslationally modified form (i.e., the initiator methionine deleted form) of the antibacterial protein without the need of a cleavage step. Without being bound to any particular theory as to why the antibacterial composition has a broad bactericidal activity against certain *Staphylococcus* species, it is believed that the antibacterial protein having the amino acid sequence of SEQ. ID. NO: 2 (the posttranslationally modified form) contributes to the broad bactericidal activity against certain *Staphylococcus* species.

The antibacterial proteins of the present invention also include variants thereof having at least 80%, 85%, 90%, 95%, 99%, or 99.5% identity to the amino acid sequence of SEQ. ID. NO: 1 or SEQ. ID. NO: 2. The amino acid sequence identity is defined herein as the percentage of amino acid residues in a candidate sequence that are identical with the amino acid residues in the antibacterial protein sequence, after aligning the sequence in the same reading frame and introducing gaps, if necessary, to achieve the maximum percent sequence identity, and not considering any conservative substitutions as part of the sequence identity.

To determine the percent identity of two amino acid sequences, the sequences are aligned for optimal comparison purposes (e.g., gaps may be introduced in the sequence of a first sequence). The amino acids at corresponding amino acid positions are then compared. When a position in the first sequence is occupied by the same amino acid as the corresponding position in the second sequence, then the molecules are identical at that position. The percent identity between the two sequences is a function of the number of identical positions shared by the sequences (i.e., % identity=# of identical positions/total # of position×100).

The antibacterial proteins having a broad bactericidal activity (lytic activity) spectrum against various *Staphylococcus* strains characteristically display a broad antibacterial spectrum against one or more *Staphylococcus* strains including *Staphylococcus arlettae*, *Staphylococcus aureus*, *Staphylococcus auricularis*, *Staphylococcus carnosus*, *Staphylococcus carprae*, *Staphylococcus chromogenes*, *Staphylococcus cohnii*, *Staphylococcus delphini*, *Staphylococcus epidermidis*, *Staphylococcus equorum*, *Staphylococcus gallinarum*, *Staphylococcus hemolyticus*, *Staphylococcus hominis*, *Staphylococcus intermedius*, *Staphylococcus kloosii*, *Staphylococcus lentus*, *Staphylococcus lugdunensis*, *Staphylococcus muscae*, *Staphylococcus pasteuri*, *Staphylococcus saprophyticus*, *Staphylococcus warneri*, and *Staphylococcus xylosus*. Furthermore, these *Staphylococcus* strains are antibiotic-sensitive or antibiotic-resistant *Staphylococcus* strain. The antibacterial activity of the antibacterial proteins having a broad bactericidal activity (lytic activity) spectrum against various *Staphylococcus* strains is independent of bacterial antibiotic susceptibility patterns.

The antibacterial composition that has bactericidal activity against various *Staphylococcus* strains and selectively induces bacteriolysis of various *Staphylococcus* strains includes an antibacterial protein consisting of the amino acid sequence of SEQ. ID. NO: 1, an antibacterial protein consisting of the amino acid sequence of SEQ. ID. NO: 2, or a mixture thereof. The antibacterial protein mixture may include 15, 16, 17, 18, 19, 20, 21, 22, 23, 24, 25, 26, 27, 28, 29, 30, 31, 32, 33, 34, or 35 mole % of the antibacterial protein consisting of the amino acid sequence of SEQ. ID. NO: 1 and 65, 66, 67, 68, 69, 70, 71, 72, 73, 74, 75, 76, 77, 78, 79, 80, 81, 82, 83, 84, or 85 mole % of the antibacterial protein consisting of the amino acid sequence of SEQ. ID. NO: 2. Preferably, the antibacterial protein mixture includes about 25 mole % of the antibacterial protein consisting of the amino acid sequence of SEQ. ID. NO: 1 and about 75 mole % of the antibacterial protein consisting of the amino acid sequence of SEQ. ID. NO: 2.

The antibacterial composition has bactericidal activity against various *Staphylococcus* strains and selectively induces bacteriolysis of various *Staphylococcus* strains, and displays a broad antibacterial spectrum against antibiotic-sensitive or antibiotic-resistant various *Staphylococcus* strains including *Staphylococcus arlettae, Staphylococcus aureus, Staphylococcus auricularis, Staphylococcus carnosus, Staphylococcus carprae, Staphylococcus chromogenes, Staphylococcus cohnii, Staphylococcus delphini, Staphylococcus epidermidis, Staphylococcus equorum, Staphylococcus gallinarum, Staphylococcus hemolyticus, Staphylococcus hominis, Staphylococcus intermedius, Staphylococcus kloosii, Staphylococcus lentus, Staphylococcus lugdunensis, Staphylococcus muscae, Staphylococcus pasteuri, Staphylococcus saprophyticus, Staphylococcus warneri,* and *Staphylococcus xylosus*.

Therefore, the antibacterial composition is effective in treating infections caused by multiple *Staphylococcus* strains. It is clinically valuable that the composition of the present invention is still effective in complex staphylococcal infections caused by multiple of *Staphylococcus* strains.

The staphylococcal infections can develop to diseases. The staphylococcal infections and the diseases caused by *Staphylococcus* are exemplified as the follows: skin infections (e.g., folliculitis, furuncles, impetigo, wound infections, scalded skin syndrome), soft-tissue infections (e.g., pyomyositis, septic bursitis, septic arthritis), toxic shock syndrome, purpura fulminans, endocarditis, osteomyelitis, pneumonia, infections related to prosthetic devices (e.g., prosthetic joints and heart valves; vascular shunts, grafts, catheters), and urinary tract infection.

The antibacterial composition of the present invention may additionally include a pharmaceutically acceptable, which is exemplified by sucrose, sorbitol, mannitol, and phosphate, but not limited thereto. The antibacterial composition of the present invention can additionally include emulsifiers, suspending agents, and stabilizer, in addition to the above ingredients, but not limited thereto.

The antibacterial composition of the present invention can be applied and administered orally or parenterally (for example, intravenous, intramuscular, hypodermic, local or peritoneal injection).

The effective dosage of the pharmaceutical composition of the present invention varies from the formulation, administration pathway, age, weight and gender of animal or human with a infections caused by *Staphylococcus*, severity of infection, diet, administration frequency and pathway, excretion and sensitivity. In general, the dosage can be determined by an experienced doctor with consideration of the goal of the treatment effect.

The antibacterial composition of the present invention can be formulated by the method that can be performed by those in the art by using a pharmaceutically acceptable carrier and/or excipient in the form of unit dose or in a multi-dose container. The formulation can be in the form of solution, suspension or emulsion in oil or water-soluble medium, extract, powder, granule, tablet or capsule. At this time, a dispersing agent or a stabilizer can be additionally included.

In this description, the term "treatment" or "treat" indicates (i) to suppress the infections caused by various *Staphylococcus* strains; and (ii) to relieve the infections caused by various *Staphylococcus* strains.

The antibacterial proteins and the antibacterial composition of the present invention differ from standard-of-care antibiotics in its potency, speed, specificity, and activity against antibiotic-resistant strains. Especially, the rapid and effective bactericidal activity against both antibiotic-sensitive and antibiotic-resistant *Staphylococcus* strains are very valuable properties considering the clinical effectivity provided by them. Unlike most antibiotics, the antibacterial proteins of the present invention and the pharmaceutical composition containing the antibacterial protein of the present invention do not require bacterial metabolism or growth for activity and are bacteriolytic upon contact. This rapid kill property makes the antibacterial composition containing the antibacterial proteins of the present invention well suited to quickly reduce the bacterial burden in infected hosts. Therefore, the antibacterial proteins and antibacterial composition of the present invention can solve the problems of antibiotic-resistance of *Staphylococcus*. In addition, the antibacterial proteins of the present invention and the antibacterial composition of the present invention are highly specific for *Staphylococcus* species and rarely lyse non-target bacteria, including commensal bacteria, which may reduce clinical complications. In general, when conventional antibiotics are used, the general residential bacteria are also damaged with carrying various side effects.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1: Preparation of the Antibacterial Composition

An expression plasmid of the antibacterial protein of the present invention was constructed by conventional subcloning a gene encoding the antibacterial protein of the present invention, which is presented by SEQ. ID. NO: 3, into the pBAD-TOPO vector (Invitrogen). *Escherichia coli* BL21 cell transformed with the resultant plasmid was used as a production host for the antibacterial protein of the present invention.

Expression of the antibacterial protein of the present invention was induced with 0.2% arabinose at an optical density at 600 nm ($OD_{600}$) of 2.0 and the induced bacterial cells were subsequently incubated for an additional 10 hours at 19° C. Bacterial cells were recovered by centrifugation (6,000×g for 20 minutes) and the resulting cell pellet was re-suspended in lysis buffer [50 mM $Na_2HPO_4$ (pH 7.5), 10 mM ethylene diamine tetra-acetic acid (EDTA), 1 mM dithiothreitol (DTT)] and disrupted using a conventional ultrasonic treatment for 5 minutes (1 second pulse with 3 seconds rest interval between pulses). Following centrifugation (13,000×g for 20 minutes), the supernatant was recovered and subjected to two-step chromatography comprising ion exchange chromatography (SP fast flow column; GE Healthcare) and hydrophobic interaction chromatography (Toyopearl PPG-600M column; Tosoh Bioscience).

To be more descriptive, the prepared production host was inoculated in a TSB (tryptic soy broth) medium (casein digest, 17 g/L; soybean digest, 3 g/L; dextrose, 2.5 g/L; NaCl, 5 g/L; dipotassium phosphate, 2.5 g/L), and incubation at 37° C. was performed. When the cell concentration reached 2.0 of $OD_{600}$, L-arabinose was added at the final concentration of 0.2% to induce the expression of the antibacterial protein. The cells were cultured at 19° C. for 10 more hours from the point of induction. The culture broth was centrifuged at 6,000×g for 20 minutes to obtain cell precipitate. The precipitate was suspended in 50 mM $Na_2HPO_4$ buffer (pH 7.5) containing 10 mM EDTA and 1 mM DTT (10 mL of buffer per 1 g of cells). Cells in the suspension were disrupted by conventional sonication. The cell lysate was centrifuged at 13,000×g for 20 minutes to remove the cell debris. The supernatant precipitate was subjected to the two-step chromatography comprising ion exchange chromatography (Buffer A: 25 mM $Na_2HPO_4$ (pH 7.5), 10 mM EDTA; Buffer B: 25 mM $Na_2HPO_4$ (pH 7.5), 10 mM EDTA, 1 M NaCl; Buffer C: 25 mM $Na_2HPO_4$ (pH 7.5), 10 mM EDTA, 50 mM NaCl, 0.5% Triton X-100; Procedure: sample loading→1.6 CV of buffer A→30 CV of buffer C→20 CV of buffer A→5 CV of 22% buffer B→elution by gradient (20 CV of 22-100% buffer B)) and hydrophobic interaction chromatography (Buffer A: 10 mM L-histidine (pH 7.5), 1 M NaCl; Buffer B: 10 mM L-histidine (pH 7.5), 1 M urea; Procedure: sample loading (sample purified by ion exchange chromatography)→10 CV of buffer A→elution by gradient (10 CV of 0-100% buffer B)). The protein solution was then filtered with 0.2 μm filter.

To determine the composition of the antibacterial proteins consisting of the amino acid sequence of SEQ. ID. NO: 1 and SEQ. ID. NO: 2, two-step analysis was performed. First, liquid chromatography (LC)-mass spectrometry (MS) was performed using a protease-treated protein sample. The protein solution obtained according to the procedure described above was subjected to buffer exchange via centrifugal filtration into 50 mM Tris-HCl buffer (pH 7.6) and diluted to a concentration of 2.5 mg/mL with 6 M urea solution. The diluted protein solution was subjected to treatment with protease. As protease, sequencing-grade modified porcine Glu-C protease (Promega, Madison, Wis., USA) was used and the protease treatment was performed according to manufacturer's protocol. After protease treatment, the protease-treated protein solution obtained was subjected to reverse-phase HPLC and Q-TOF-MS. Through peak analysis, the HPLC and MS peaks corresponding to peptide fragment of MAKTQAE originated from the antibacterial protein consisting of the amino acid sequence of SEQ. ID. NO: 1 and peptide fragment of AKTQAE originated from the antibacterial protein consisting of the amino acid sequence of SEQ. ID. NO: 2 were identified based on the estimated protease digestion pattern and mass calculations. In addition, the HPLC and MS peaks were confirmed by comparing the peak pattern obtained using chemically synthesized peptides (MAKTQAE and AKTQAE) as samples. Subsequently, the composition ratio of the antibacterial protein consisting of the amino acid sequence of SEQ. ID. NO: 1 in the antibacterial protein preparation was determined by reverse-phase HPLC analysis with the protease-treated protein sample and chemically synthesized peptides (MAKTQAE and AKTQAE) based on correlation of concentration of peptide and peak area corresponding to it. As results of analysis with three batches of antibacterial protein, the composition ratio of the antibacterial protein consisting of the amino acid sequence of SEQ. ID. NO: 1 was determined to be 25, 27 and 29 mole %, and the composition ratio of the antibacterial protein consisting of the amino acid sequence of SEQ. ID. NO: 2 was determined to be 75, 73, and 72 mole %, respectively.

Example 2: Preparation of the Pharmaceutical Composition

A pharmaceutical composition for the treatment of staphylococcal infections comprising the antibacterial proteins of the present invention was prepared by buffer exchange. In this preparation, the protein solution prepared in Example 1 was used and the buffer exchange was conducted by performing conventional diafiltration to formulation buffer (1.56 g/L L-histidine (pH 6.0), 50 g/L D-sorbitol, 1.47 g/L $CaCl_2.2H_2O$, and 1 g/L poloxamer 188).

Example 3: Examination of Antibacterial Activity Against *Staphylococcus* Strains To evaluate the antibacterial activity of the pharmaceutical composition of the present invention, an antibacterial activity test was performed using the pharmaceutical composition prepared in Example 2. As an antibacterial activity test, spot-on-lawn assay and turbidity reduction assay were performed.

The spot-on-lawn assay was performed as the follows: TSA (Tryptic Soy Agar; pancreatic digest of casein, 17 g/L; papaic digest of soybean, 3 g/L; sodium chloride, 5 g/L; agar, 15 g/L) plates were overlaid with 2 mL of a culture of each *Staphylococcus* strain (McFarland standard was 0.5). After air-drying, the plates were incubated overnight at 37° C. After incubation, 10 μL of dilution of the pharmaceutical composition prepared in Example 2 (final concentration of antibacterial protein: 1 μg/mL) was spotted onto the bacterial lawn, and the plates were further incubated at 37° C. for 30 minutes. After incubation, the formation of a clear zone (lysis halo) indicating the bactericidal effect of the pharmaceutical composition was examined.

The turbidity reduction assay was performed as the follows: the pharmaceutical composition prepared in Example 2 was added to each suspension of *Staphylococcus* strain ($OD_{600}$=0.5) in 10 mM phosphate-buffered saline (PBS) (pH 7.2) to be a final antibacterial protein concentration of 0.1 μg/mL (in some cases, 0.5 μg/mL or 1.0 μg/mL was also used). Changes in bacterial cell density ($OD_{600}$) were recorded every 30 seconds for 15 minutes. From this experiment, $TOD_{50}$ (a one-half log drop in the initial concentration of viable bacteria in minutes) was obtained.

In these experiments, the following strains were used as the *Staphylococcus* strains.

TABLE 1

Test Strains

| No. | Species | Strain information | Antibiotic resistance information |
|---|---|---|---|
| 1 | Staphylococcus arlettae | KCTC 3588 (ATCC 43957) | Not available |
| 2 | Staphylococcus aureus | ATCC 35556 | Not available |
| 3 | Staphylococcus auricularis | KCTC 3584 (ATTC 33753) | Not available |
| 4 | Staphylococcus carnosus | KCTC 3580 (ATCC 51365) | Not available |
| 5 | Staphylococcus carprae | KCTC 3583 (ATCC 35538) | Not available |
| 6 | Staphylococcus chromogenes | KCTC 3579 (ATCC 43764) | Not available |
| 7 | Staphylococcus cohnii | KCTC 3574 (ATCC 49330) | Not available |
| 8 | Staphylococcus delphini | KCTC 3592 (ATCC 49171) | Not available |
| 9 | Staphylococcus epidermidis | CCARM 3751 | Ampicillin resistant; Clindamycin resistant; Erythromycin resistant; Gentamycin resistant |
| 10 | Staphylococcus equorum | KCTC 3589 (ATCC 43958) | Not available |
| 11 | Staphylococcus gallinarum | KCTC 3585 (ATCC 35539) | Not available |
| 12 | Staphylococcus hemolyticus | CCARM 3733 | Not available |
| 13 | Staphylococcus hominis | CCARM 3732 | Ciprofloxacin resistant |

TABLE 1-continued

Test Strains

| No. | Species | Strain information | Antibiotic resistance information |
|---|---|---|---|
| 14 | Staphylococcus intermedius | KCTC 3344 (ATCC 29663) | Not available |
| 15 | Staphylococcus kloosii | KCTC 3590 (ATCC 43959) | Not available |
| 16 | Staphylococcus lentus | KCTC 3577 (ATCC 29070) | Not available |
| 17 | Staphylococcus lugdunensis | CCARM 3734 | Not available |
| 18 | Staphylococcus muscae | KCTC 3576 (ATCC 49910) | Not available |
| 19 | Staphylococcus pasteuri | KCTC 13167 | Not available |
| 20 | Staphylococcus saprophyticus | CCARM 3736 | Not available |
| 21 | Staphylococcus warneri | KCTC 3340 (ATCC 27836) | Not available |
| 22 | Staphylococcus xylosus | KCTC 3342 (ATCC 29971) | Not available |

Figure 2:
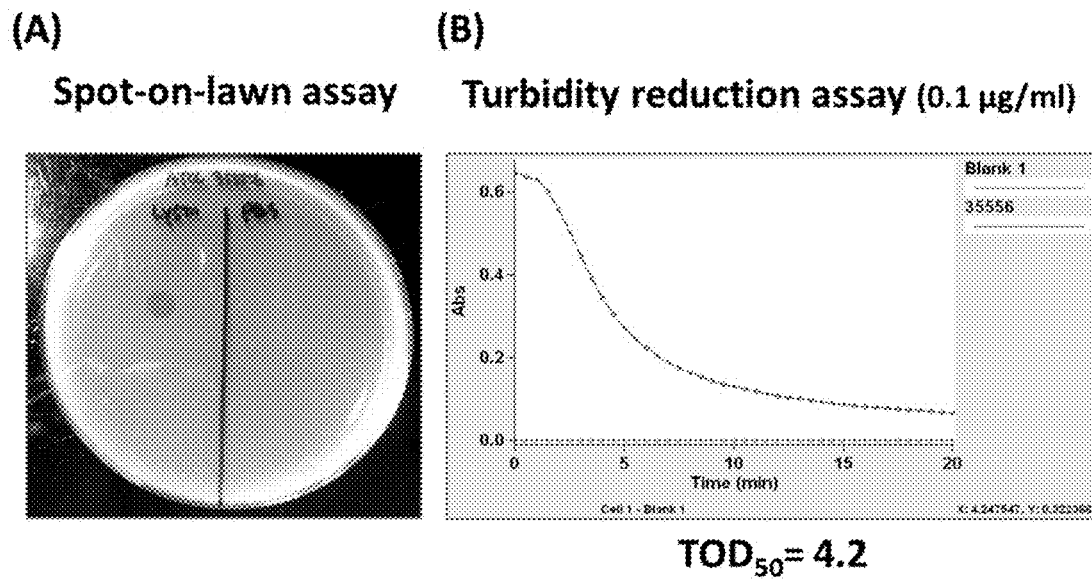
FIG. 2 is a result showing the effective bactericidal activity against *Staphylococcus aureus*. (A) spot-on-lawn assay and (B) turbidity reduction assay.
Figure 3:
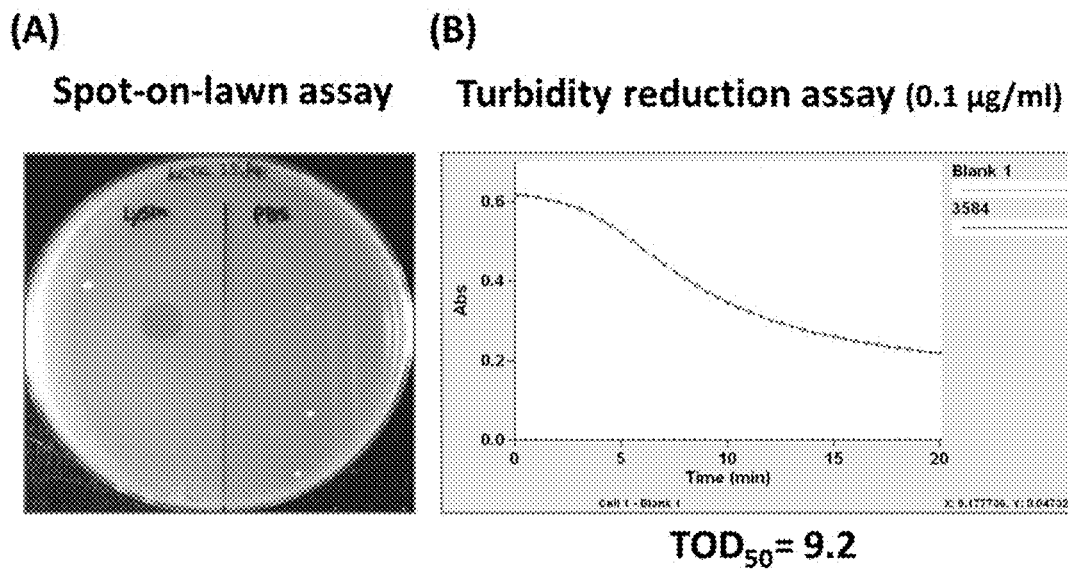
FIG. 3 is a result showing the effective bactericidal activity against *Staphylococcus auricularis*. (A) spot-on-lawn assay and (B) turbidity reduction assay.
Figure 4:
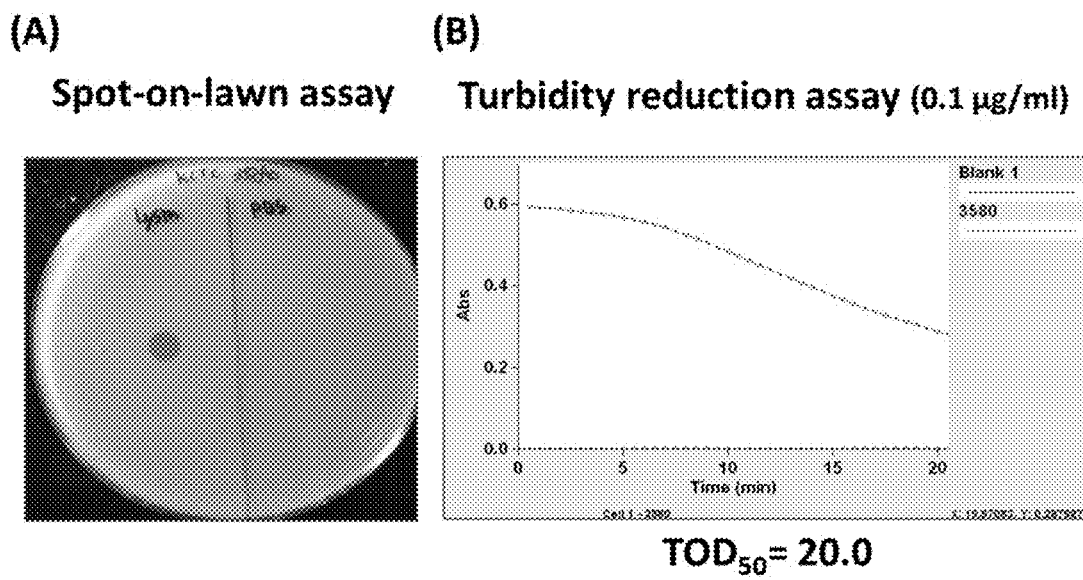
FIG. 4 is a result showing the effective bactericidal activity against *Staphylococcus carnosus*. (A) spot-on-lawn assay and (B) turbidity reduction assay.
Figure 5:
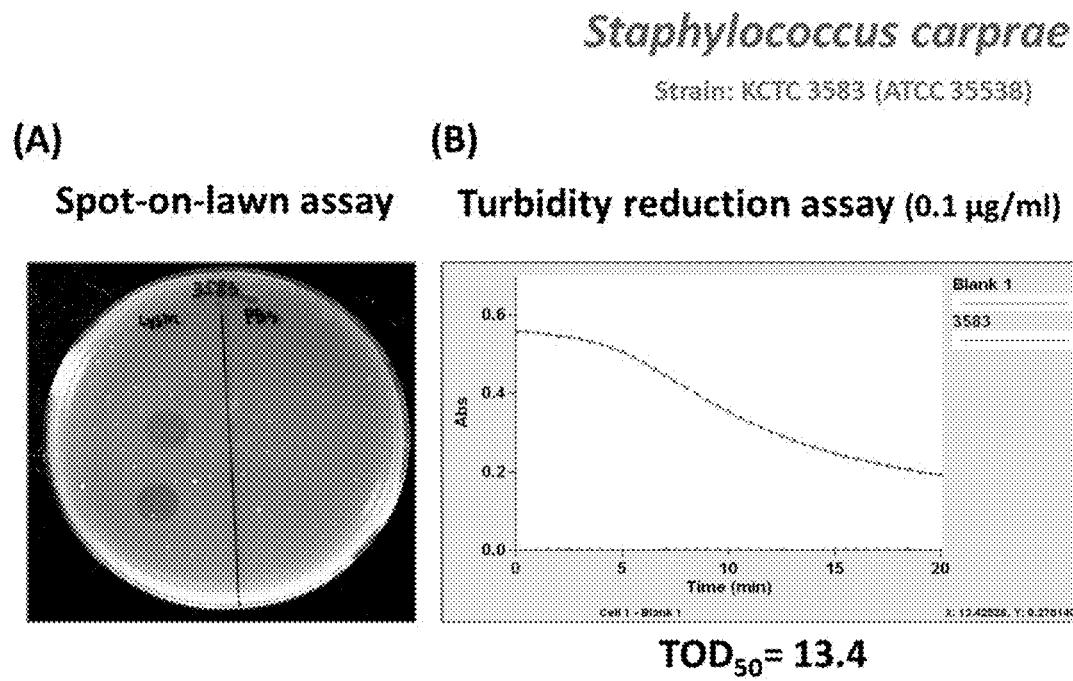
FIG. 5 is a result showing the effective bactericidal activity against *Staphylococcus carprae*. (A) spot-on-lawn assay and (B) turbidity reduction assay.
Figure 6:
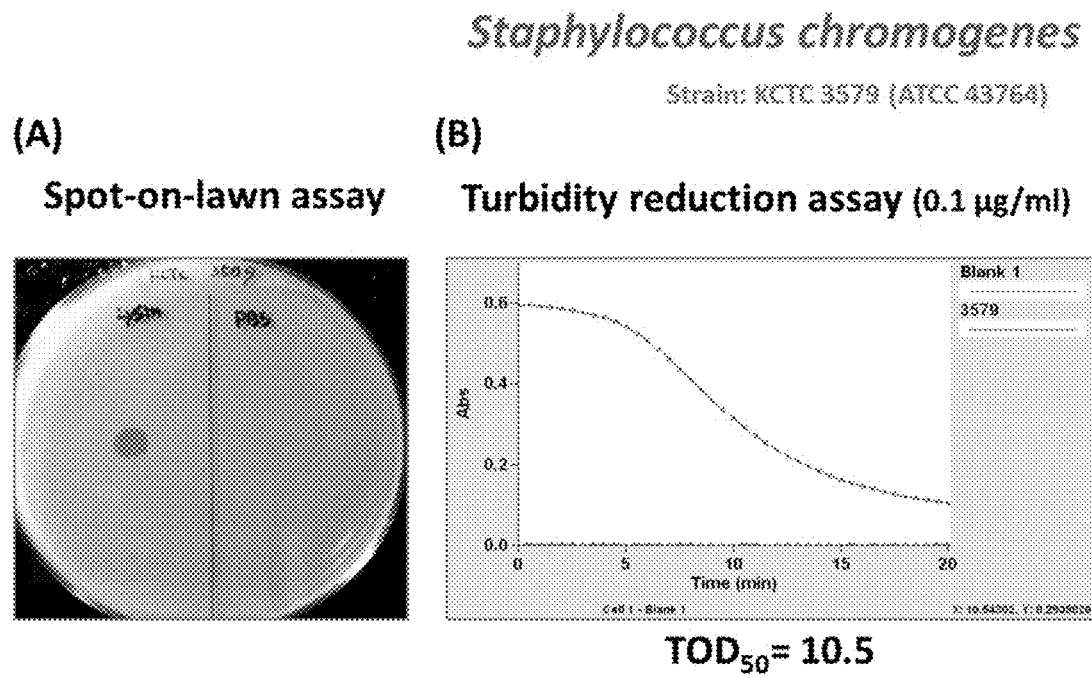
FIG. 6 is a result showing the effective bactericidal activity against *Staphylococcus chromogenes*. (A) spot-on-lawn assay and (B) turbidity reduction assay.
Figure 7:
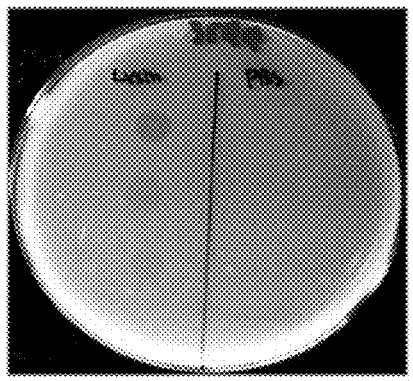
FIG. 7 is a result showing the effective bactericidal activity against *Staphylococcus cohnii*. (A) spot-on-lawn assay and (B) turbidity reduction assay.
Figure 7:
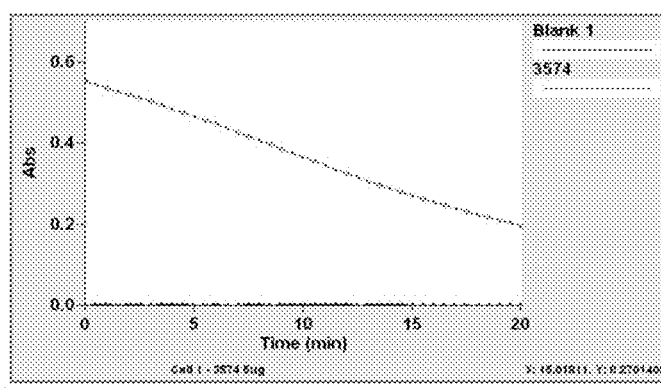
Figure 8:
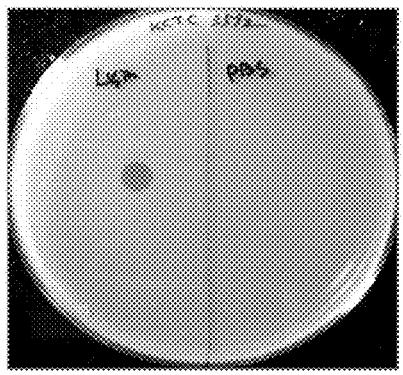
FIG. 8 is a result showing the effective bactericidal activity against *Staphylococcus delphini*. (A) spot-on-lawn assay and (B) turbidity reduction assay.
Figure 8:
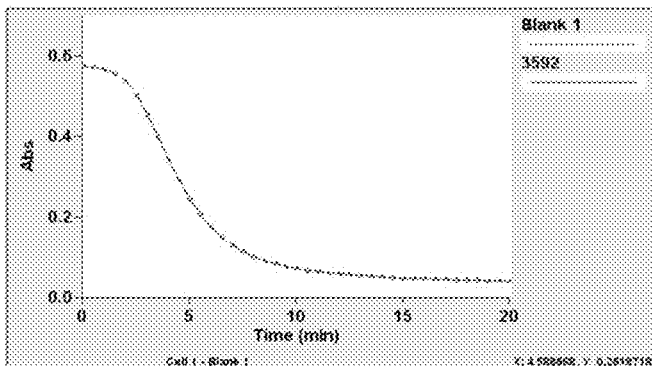
Figure 9:
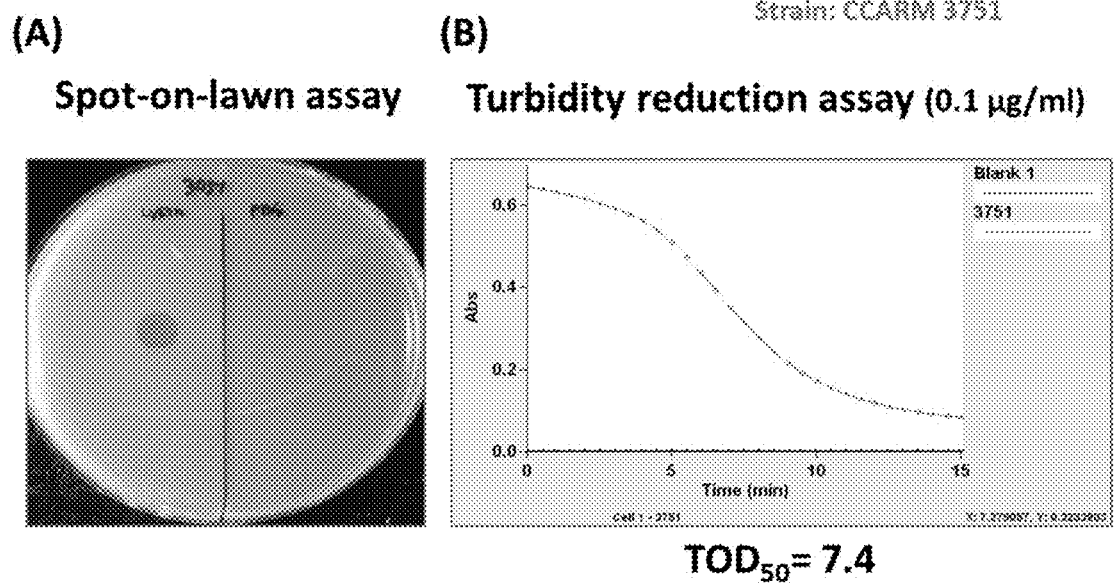
FIG. 9 is a result showing the effective bactericidal activity against *Staphylococcus epidermidis*. (A) spot-on-lawn assay and (B) turbidity reduction assay.
Figure 10:
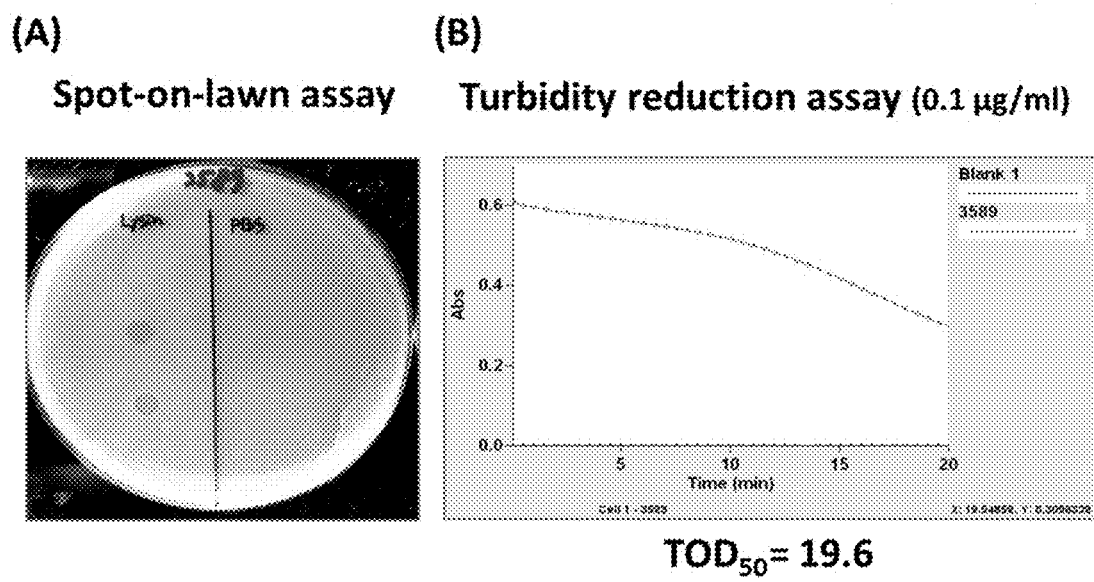
FIG. 10 is a result showing the effective bactericidal activity against *Staphylococcus equorum*. (A) spot-on-lawn assay and (B) turbidity reduction assay.
Figure 11:
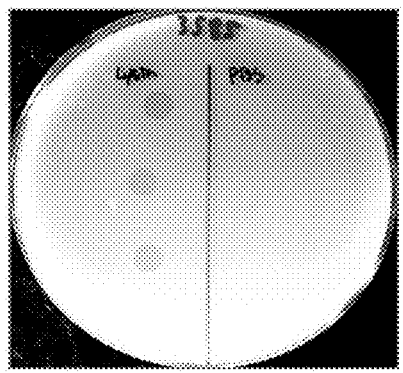
FIG. 11 is a result showing the effective bactericidal activity against *Staphylococcus gallinarum*. (A) spot-on-lawn assay and (B) turbidity reduction assay.
Figure 11:
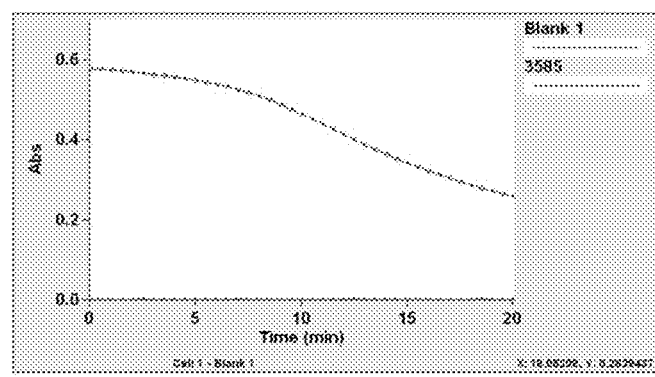
Figure 12:
FIG. 12 is a result showing the effective bactericidal activity against *Staphylococcus hemolyticus*. (A) spot-on-lawn assay and (B) turbidity reduction assay.
Figure 12:
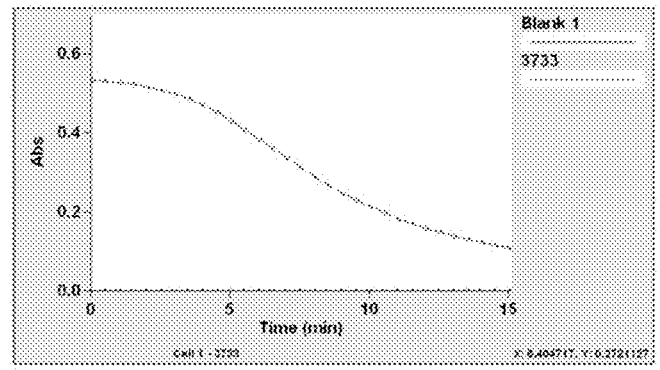
Figure 13:
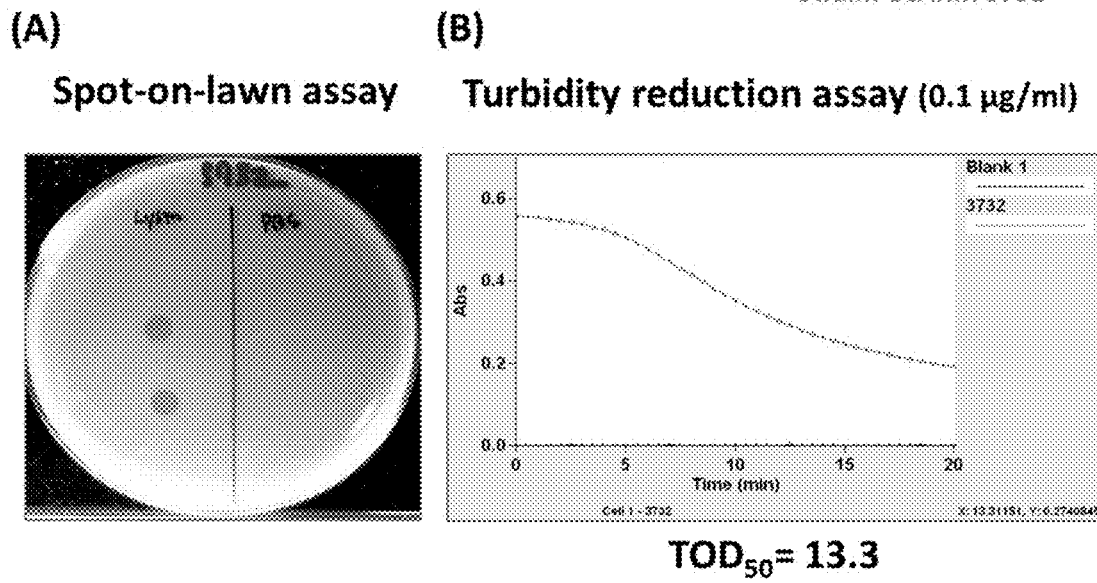
FIG. 13 is a result showing the effective bactericidal activity against *Staphylococcus hominis*. (A) spot-on-lawn assay and (B) turbidity reduction assay.
Figure 14:
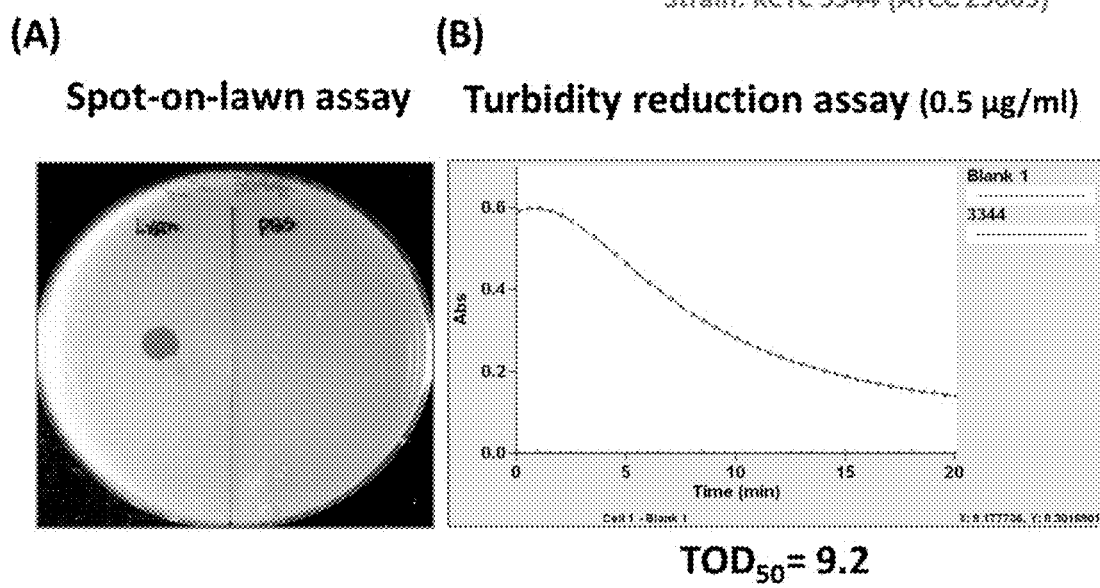
FIG. 14 is a result showing the effective bactericidal activity against *Staphylococcus intermedius*. (A) spot-on-lawn assay and (B) turbidity reduction assay.
Figure 15:
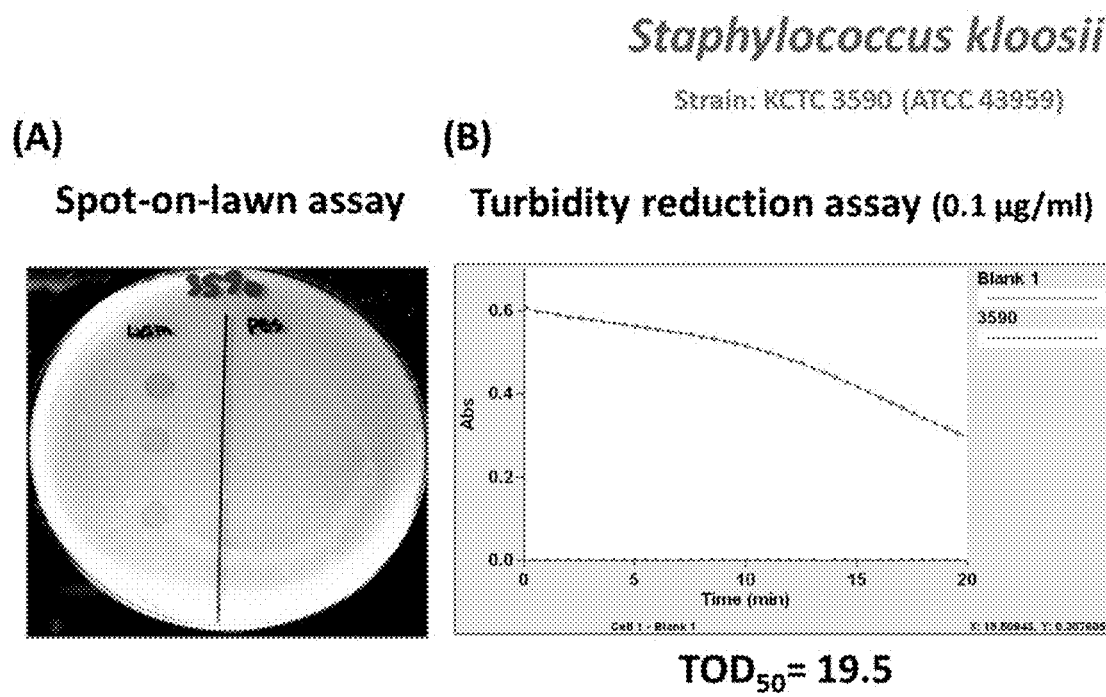
FIG. 15 is a result showing the effective bactericidal activity against *Staphylococcus kloosii*. (A) spot-on-lawn assay and (B) turbidity reduction assay.
Figure 16:
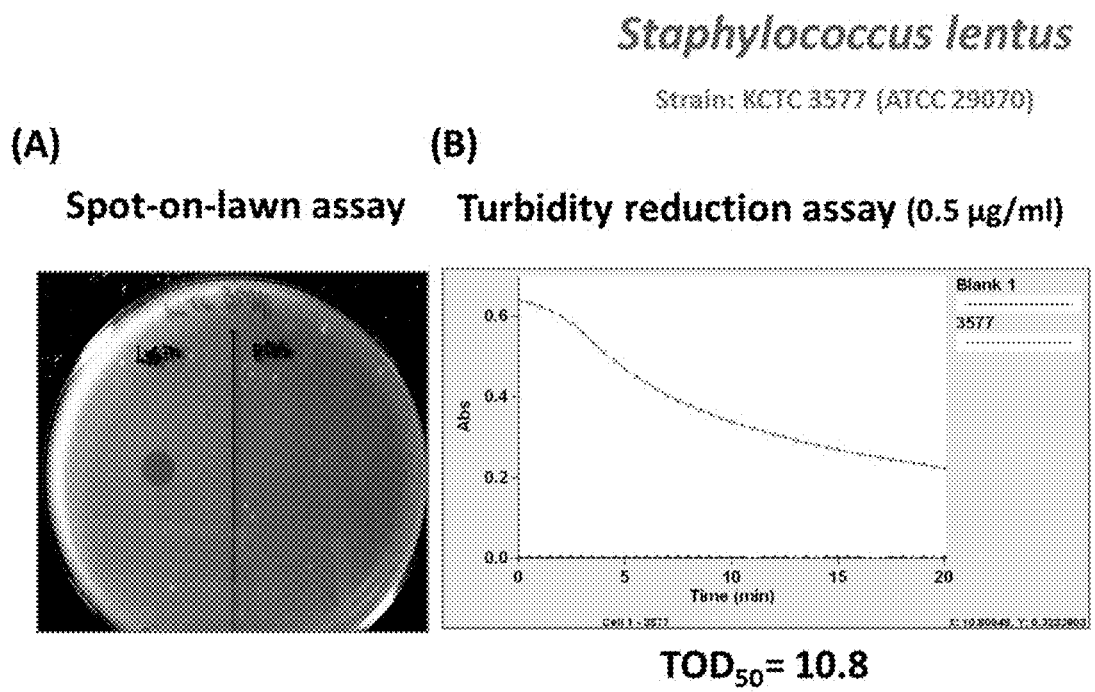
FIG. 16 is a result showing the effective bactericidal activity against *Staphylococcus lentus*. (A) spot-on-lawn assay and (B) turbidity reduction assay.
Figure 17:
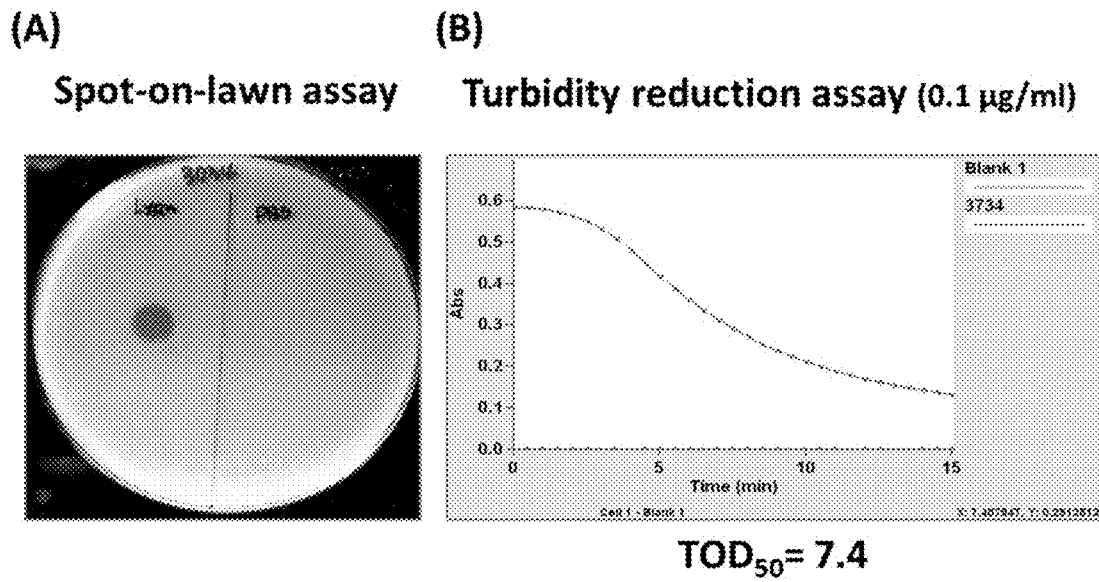
FIG. 17 is a result showing the effective bactericidal activity against *Staphylococcus lugdunensis*. (A) spot-on-lawn assay and (B) turbidity reduction assay.
Figure 18:
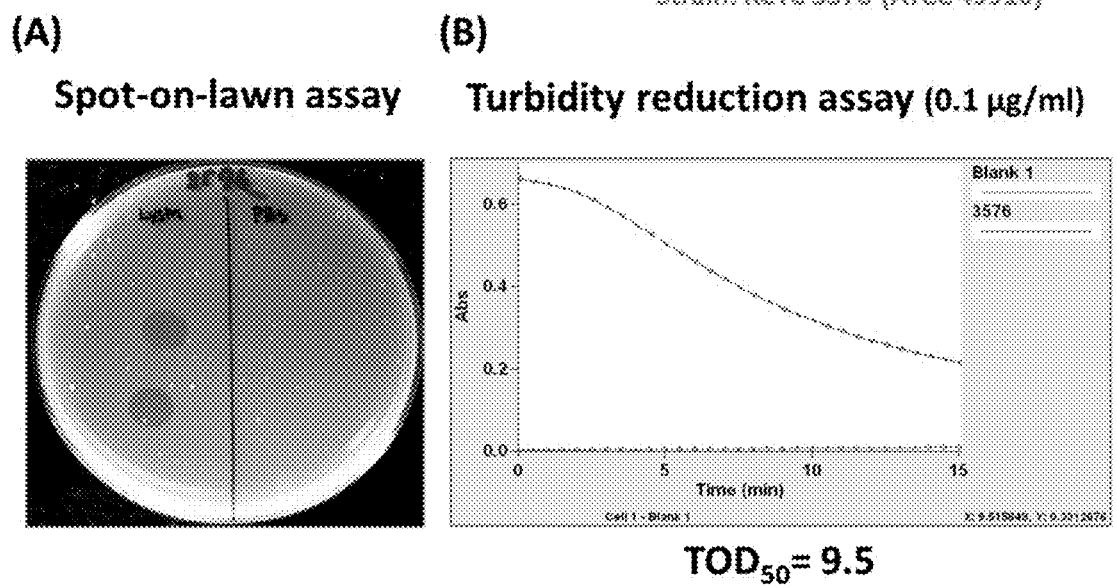
FIG. 18 is a result showing the effective bactericidal activity against *Staphylococcus muscae*. (A) spot-on-lawn assay and (B) turbidity reduction assay.
Figure 19:
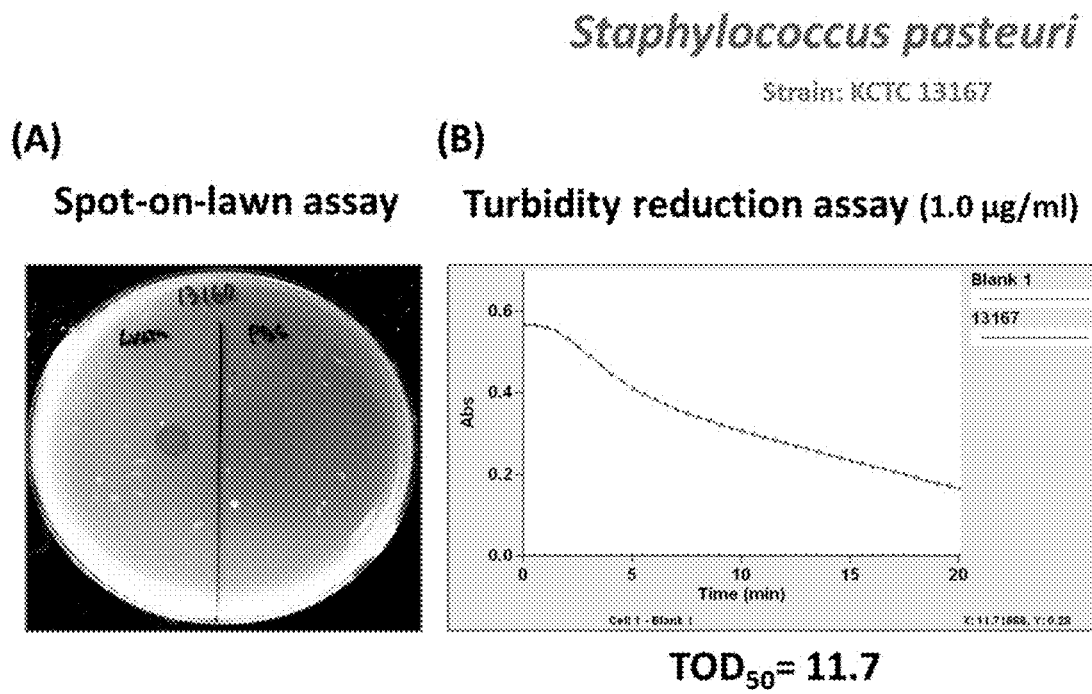
FIG. 19 is a result showing the effective bactericidal activity against *Staphylococcus pasteuri*. (A) spot-on-lawn assay and (B) turbidity reduction assay.
Figure 20:
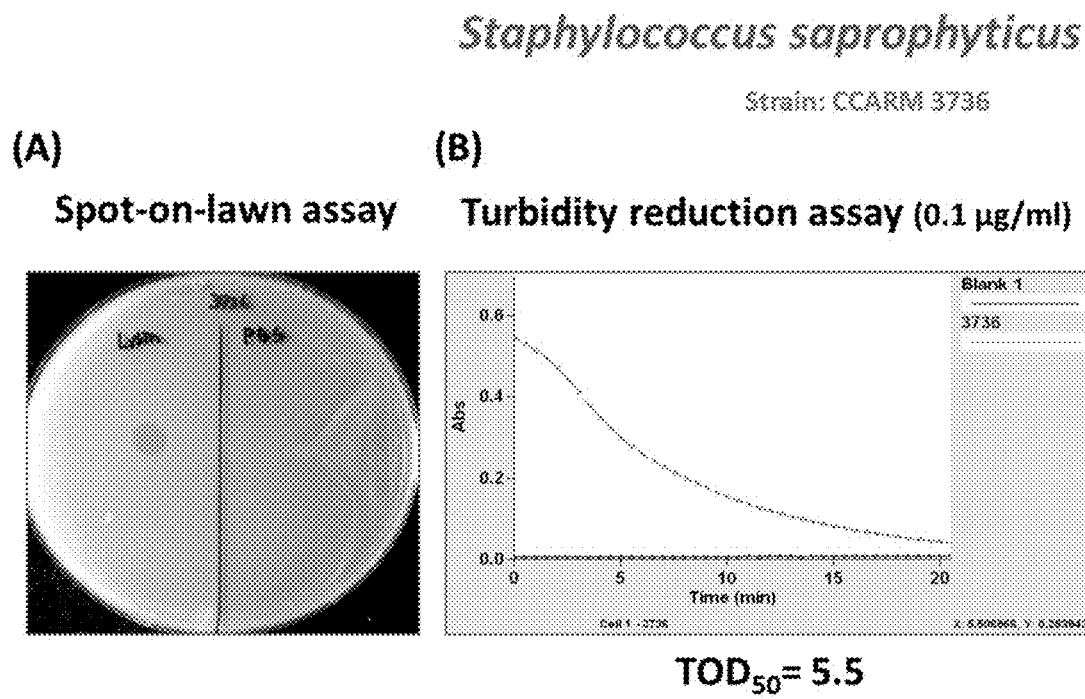
FIG. 20 is a result showing the effective bactericidal activity against *Staphylococcus saprophyticus*. (A) spot-on-lawn assay and (B) turbidity reduction assay.
Figure 21:
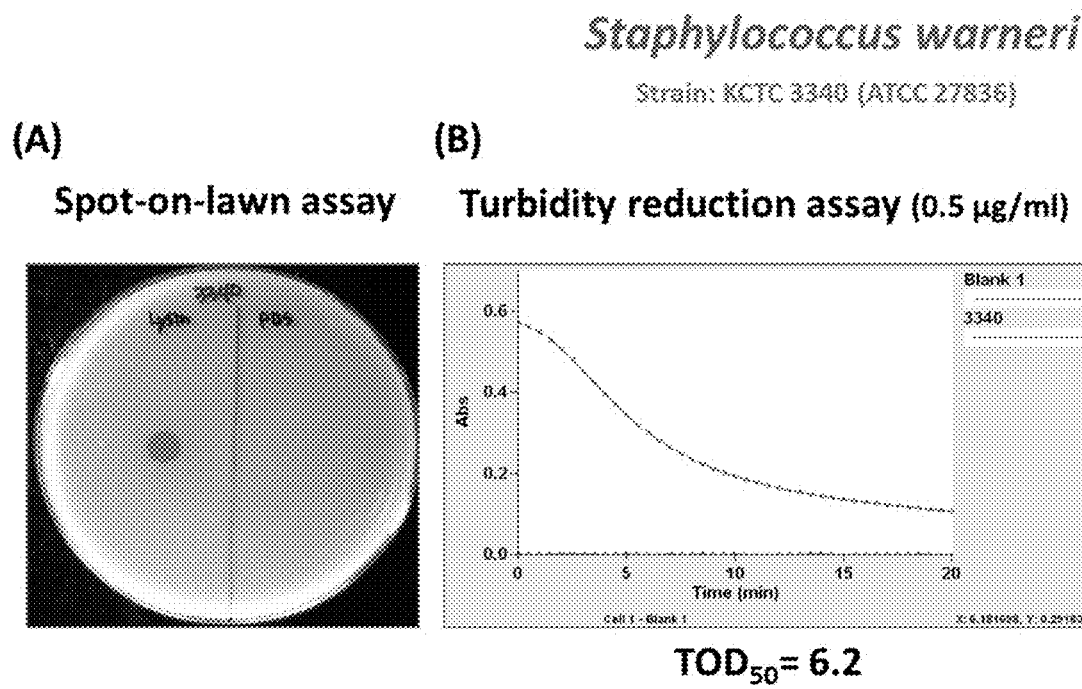
FIG. 21 is a result showing the effective bactericidal activity against *Staphylococcus warneri*. (A) spot-on-lawn assay and (B) turbidity reduction assay.
Figure 22:
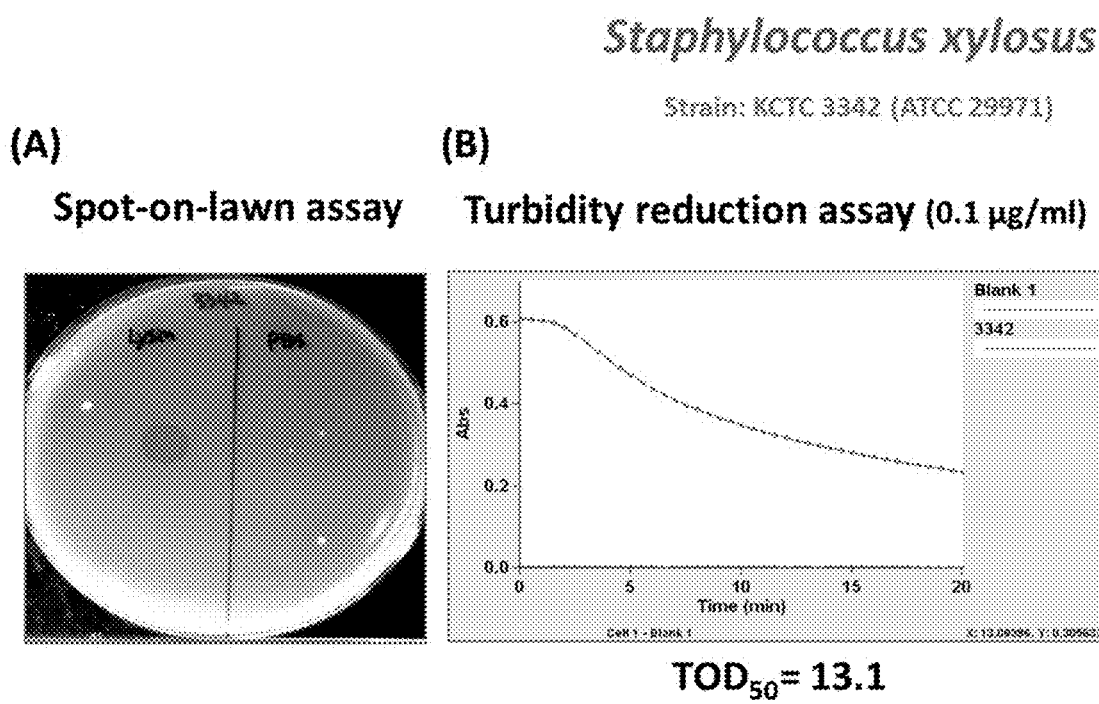
FIG. 22 is a result showing the effective bactericidal activity against *Staphylococcus xylosus*. (A) spot-on-lawn assay and (B) turbidity reduction assay.

ATCC: American Type Culture Collection;
CCARM: Culture Collection of Antimicrobial Resistant Microbes;
KCTC: Korean Collection for Type Culture The results are presented in FIGS. 1-22. The results shown in FIGS. 1-22 obviously indicate that the pharmaceutical composition of the present invention (i.e., the antibacterial composition of the present invention or the antibacterial proteins of the present invention) has rapid and effective bactericidal activity against various *Staphylococcus* strains. $TOD_{50}$ of the pharmaceutical composition was less than 20 minutes against almost all *Staphylococcus* strains tested.

In the meantime, the antibacterial activity of the pharmaceutical composition of the present invention against non-*Staphylococcus* strains was examined. As non-*Staphylococcus* strains, 5 *Enterococcus faecalis* strains, 5 *Enterococcus faecium* strains, 2 *Streptococcus mitis* strains, 1 *Streptococcus uberis* strain, 10 *Escherichia coli* strains, and 7 *Salmonella* strains were tested. As a result, the pharmaceutical composition of the present invention did not have the antibacterial activity against these non-*Staphylococcus* strains tested (Table 2).

TABLE 2

Antibacterial activity against non-*Staphylococcus* strains

| Bacteria tested | | Spot-on-lawn assay | Turbidity reduction assay |
|---|---|---|---|
| Enterococcus faecalis | Strain 1 | — | — |
| | Strain 2 | — | — |
| | Strain 3 | — | — |
| | Strain 4 | — | — |
| | Strain 5 | — | — |
| Enterococcus faecium | Strain 1 | — | — |
| | Strain 2 | — | — |
| | Strain 3 | — | — |
| | Strain 4 | — | — |
| | Strain 5 | — | — |
| Streptococcus mitis | Strain 1 | — | — |
| | Strain 2 | — | — |
| Streptococcus uberis | Strain 1 | — | — |
| Escherichia coli | Strain 1 | — | — |
| | Strain 2 | — | — |
| | Strain 3 | — | — |
| | Strain 4 | — | — |
| | Strain 5 | — | — |

TABLE 2-continued

Antibacterial activity against non-*Staphylococcus* strains

| Bacteria tested | | Spot-on-lawn assay | Turbidity reduction assay |
|---|---|---|---|
| | Strain 6 | — | — |
| | Strain 7 | — | — |
| | Strain 8 | — | — |
| | Strain 9 | — | — |
| | Strain 10 | — | — |
| Salmonella | Strain 1 | — | — |
| | Strain 2 | — | — |
| | Strain 3 | — | — |
| | Strain 4 | — | — |
| | Strain 5 | — | — |
| | Strain 6 | — | — |
| | Strain 7 | — | — |

—No activity.

Therefore, it is concluded that the pharmaceutical composition of the present invention was *Staphylococcus* specific and has a broad antibacterial spectrum within *Staphylococcus*, suggesting that the pharmaceutical composition of the present invention can be used as a therapeutic agent for staphylococcal infections.

Example 4: Therapeutic Effect of the Pharmaceutical Composition on Single Staphylococcal Infection Therapeutic effect of the pharmaceutical composition of the present invention on single staphylococcal infections was investigated using animal model. In this experiment, *Staphylococcus epidermidis* and *Staphylococcus hemolyticus* were selected as model *Staphylococcus* strains.

For *Staphylococcus epidermidis* experiment, female ICR mice [specific pathogen-free (SPF) grade] weighing 23 g±20% (5 weeks of age) were used. In total, 20 mice divided into two groups (10 mice per group) were injected intravenously with inocula of *Staphylococcus epidermidis* strain CCARM 3751 ($1\times10^8$ CFU/mouse). To the animal of one group (i.e., control group), only formulation buffer (1.56 g/L L-histidine (pH 6.0), 50 g/L D-sorbitol, 1.47 g/L $CaCl_2.2H_2O$, and 1 g/L poloxamer 188) was administered intravenously three times at 30 minutes, 12 hours, and 24 hours after the bacterial challenge. To the animal of the other group (i.e., treatment group), the pharmaceutical composition prepared in Example 2 was administered intravenously (dose: 25 mg/kg) three times at 30 minutes, 12 hours, and 24 hours after the bacterial challenge. The number of dead mice was recorded and clinical signs were observed daily. The ability of the pharmaceutical composition of the present invention to eradicate bacteria from the bloodstream was examined using blood collected 5 days after the bacterial challenge (experimental endpoint) by conventional colony counting.

For *Staphylococcus hemolyticus* experiment, female ICR mice [specific pathogen-free (SPF) grade] weighing 22 g±20% (5 weeks of age) were used. In total, 20 mice divided into two groups (10 mice per group) were injected intravenously with inocula of *Staphylococcus hemolyticus* strain CCARM 3733 ($1\times10^8$ CFU/mouse). To the animal of one group (i.e., control group), only formulation buffer (1.56 g/L L-histidine (pH 6.0), 50 g/L D-sorbitol, 1.47 g/L $CaCl_2.2H_2O$, and 1 g/L poloxamer 188) was administered intravenously three times at 30 minutes, 12 hours, and 24 hours after the bacterial challenge. To the animal of the other group (i.e., treatment group), the pharmaceutical composition prepared in Example 2 was administered intravenously (dose: 25 mg/kg) three times at 30 minutes, 12 hours, and 24 hours after the bacterial challenge. The number of dead mice was recorded and clinical signs were observed daily. The ability of the pharmaceutical composition of the present invention to eradicate bacteria from the bloodstream was examined using blood collected 5 days after the bacterial challenge (experimental endpoint) by conventional colony counting.

As results, obvious therapeutic effects were observed. Two experiments showed similar results. Regarding clinical signs, although mice in treatment group were normal for the entire experimental period, mice in control group showed various clinical signs beginning 2 days after the bacterial challenge, including erythema of the lid margin, decreased locomotor activity, loss of fur, ptosis, piloerection and circling. An intravenous injection of the pharmaceutical composition of the present invention significantly increased the survival rate (Table 3).

TABLE 3

Mortality in single *staphylococcal* infection model experiments

| Experiment | Group | Number of deaths Days after bacterial challenge | | | | | No. dead/ No. chal- lenged | Mortality (%) |
|---|---|---|---|---|---|---|---|---|
| | | 1 | 2 | 3 | 4 | 5 | | |
| S. epidermidis | Control | 0 | 3 | 2 | 1 | 0 | 6/10 | 60 |
| | Treatment | 0 | 0 | 0 | 0 | 0 | 0/10 | 0 |
| S. hemolyticus | Control | 0 | 2 | 1 | 1 | 0 | 4/10 | 40 |
| | Treatment | 0 | 0 | 0 | 0 | 0 | 0/10 | 0 |

In addition, an intravenous injection of the pharmaceutical composition of the present invention significantly reduced the bacterial counts in blood. The mean CFU/mL was $>1 \times 10^6$ in serum collected from the mice of the control group in the *Staphylococcus epidermidis* experiment and $>1 \times 10^5$ in serum from the mice of the control group in the *Staphylococcus hemolyticus* experiment, whereas no bacterial colonies were observed in mice of both treatment groups.

From the above results, it was confirmed that the pharmaceutical composition prepared according to the present invention were effective in treating single staphylococcal infections. Therefore, it can be concluded that the pharmaceutical composition of the present invention can be efficiently used for the treatment of staphylococcal infections.

Example 5: Therapeutic Effect of the Pharmaceutical Composition on Multiple Staphylococcal Infection Therapeutic effect of the pharmaceutical composition of the present invention on multiple staphylococcal infections was investigated using animal model. In this experiment, *Staphylococcus epidermidis*, *Staphylococcus lugdunensis* and *Staphylococcus warneri* were selected as model *Staphylococcus* strains.

Female ICR mice [specific pathogen-free (SPF) grade] weighing 23 g±20% (5 weeks of age) were used. In total, 20 mice divided into two groups (10 mice per group) were injected intravenously with mixed inocula of *Staphylococcus epidermidis* CCARM 3751, *Staphylococcus lugdunensis* CCARM 3734 and *Staphylococcus warneri* KCTC 3340 (ATCC 27836) ($1 \times 10^8$ CFU each/mouse). To the animal of one group (i.e., control group), only formulation buffer (1.56 g/L L-histidine (pH 6.0), 50 g/L D-sorbitol, 1.47 g/L $CaCl_2 \cdot 2H_2O$, and 1 g/L poloxamer 188) was administered intravenously three times at 30 minutes, 12 hours, and 24 hours after the bacterial challenge. To the animal of the other group (i.e., treatment group), the pharmaceutical composition prepared in Example 2 was administered intravenously (dose: 25 mg/kg) three times at 30 minutes, 12 hours, and 24 hours after the bacterial challenge. The number of dead mice was recorded and clinical signs were observed daily. The ability of the pharmaceutical composition of the present invention to eradicate bacteria from the bloodstream was examined using blood collected 5 days after the bacterial challenge (experimental endpoint) by conventional colony counting.

As results, obvious therapeutic effects were observed. Regarding clinical signs, although mice in treatment group were normal for the entire experimental period, mice in control group showed various clinical signs, including erythema of the lid margin, decreased locomotor activity, loss of fur, ptosis, and piloerection. An intravenous injection of the pharmaceutical composition of the present invention significantly increased the survival rate (shown in Table 4).

TABLE 4

Mortality in multiple *staphylococcal* infection model experiment

| Group | Number of deaths Days after bacterial challenge | | | | | No. dead/ No. challenged | Mortality (%) |
|---|---|---|---|---|---|---|---|
| | 1 | 2 | 3 | 4 | 5 | | |
| Control | 0 | 2 | 2 | 2 | 0 | 6/10 | 60 |
| Treatment | 0 | 0 | 0 | 0 | 0 | 0/10 | 0 |

In addition, an intravenous injection of the pharmaceutical composition of the present invention significantly reduced the bacterial counts in blood. The mean CFU/mL was $>1 \times 10^6$ in serum collected from the mice of the control group, whereas no bacterial colonies were observed in mice of treatment group.

From the above results, it was confirmed that the pharmaceutical composition prepared according to the present invention was effective in treating multiple staphylococcal infections. Therefore, it can be concluded that the pharmaceutical composition of the present invention can be efficiently used for the treatment of staphylococcal infections.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A method of treating staphylococcal infections comprising:
administering to a subject an effective amount of an antibacterial composition,
wherein the antibacterial composition has a broad bactericidal activity against all following *Staphylococcus* species: *Staphylococcus arlettae, Staphylococcus aureus, Staphylococcus auricularis, Staphylococcus carnosus, Staphylococcus carprae, Staphylococcus chromogenes, Staphylococcus cohnii, Staphylococcus delphini, Staphylococcus epidermidis, Staphylococcus equorum, Staphylococcus gallinarum, Staphylococcus hemolyticus, Staphylococcus hominis, Staphylococcus intermedius, Staphylococcus kloosii, Staphylococcus lentus, Staphylococcus lugdunensis, Staphylococcus muscae, Staphylococcus pasteuri, Staphylococcus saprophyticus, Staphylococcus warneri,* and *Staphylococcus xylosus,*
wherein the antibacterial composition includes a mixture of 15-35 mole % of a first isolated antibacterial protein consisting of the amino acid sequence as set forth in SEQ. ID. NO: 1 and 55-85% of a second isolated recombinant antibacterial protein consisting of the amino acid sequence as set forth in SEQ. ID. NO: 2; and
wherein the antibacterial composition further includes at least one selected from the group consisting of L-histidine, D-sorbitol, $CaCl_2$, and poloxamer 188.

2. The method of claim 1, wherein the mixture includes 25 mole % of the first isolated antibacterial protein and 75 mole % of the second isolated antibacterial protein.

3. The method of claim 1, wherein the staphylococcal infections are skin infections, soft-tissue infections, toxic shock syndrome, purpura fulminans, endocarditis, osteomyelitis, pneumonia, infections related to prosthetic devices, or urinary tract infections.

4. The method of claim 3, wherein the skin infections are folliculitis, furuncles, impetigo, wound infections, or scalded skin syndrome.

5. The method of claim 3, wherein the soft-tissue infections are pyomyositis, septic bursitis, or septic arthritis.

6. The method of claim 3, wherein the prosthetic devices are prosthetic joints and heart valves, vascular shunts, grafts, or catheters.

7. The method of claim 1, further comprising:
preparing the mixture by a process that includes a culture step in which induced bacterial cells are incubated at 19° C. without a cleavage step.

* * * * *